(12) United States Patent
Najafi et al.

(10) Patent No.: US 10,022,054 B2
(45) Date of Patent: Jul. 17, 2018

(54) IMPLANTABLE WIRELESS SENSOR SYSTEMS

(75) Inventors: Nader Najafi, Ann Arbor, MI (US); Jacek Rysard Baranowski, Linköping (SE); David Joseph Goetzinger, Livonia, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 1181 days.

(21) Appl. No.: 13/492,185

(22) Filed: Jun. 8, 2012

(65) Prior Publication Data
US 2013/0144379 A1 Jun. 6, 2013

Related U.S. Application Data

(60) Provisional application No. 61/494,536, filed on Jun. 8, 2011.

(51) Int. Cl.
*A61B 5/00* (2006.01)
*A61B 5/0205* (2006.01)
(Continued)

(52) U.S. Cl.
CPC ........ *A61B 5/02055* (2013.01); *A61B 5/0024* (2013.01); *A61B 5/0031* (2013.01);
(Continued)

(58) Field of Classification Search
CPC . A61B 5/02055; A61B 5/0024; A61B 5/0031; A61B 5/02158; A61B 5/042;
(Continued)

(56) References Cited

U.S. PATENT DOCUMENTS

| 4,685,446 A | 8/1987 | Choy |
| 4,925,443 A | 5/1990 | Heilman et al. |

(Continued)

FOREIGN PATENT DOCUMENTS

| EP | 1595574 A1 | 11/2005 |
| WO | WO 01/76472 A1 | 10/2001 |
| WO | WO05/18737 A1 | 3/2005 |

OTHER PUBLICATIONS

Extended European Search Report for European Patent Application No. 12796727.1, dated Apr. 10, 2015.
(Continued)

*Primary Examiner* — John R Downey
*Assistant Examiner* — Shirley Jian
(74) *Attorney, Agent, or Firm* — Cooley LLP

(57) ABSTRACT

In some embodiments, a cardiac monitoring system includes multiple sensors configured for implantation in a cardiovascular system of a user. Each sensor includes a sensing unit configured to be disposed in sensory communication with the location for measuring a biological parameter in the at least one heart chamber. The sensing unit is also configured to generate a sensory signal associated with the biological parameter. Each sensor also includes a wireless transceiver configured to receive the sensory signal from the sensing unit. The wireless transceiver is further configured to wirelessly transmit the sensory signal to an external processing device disposed outside a body of the user. The external processing device monitors, based on the sensory signal received from at least two sensors from the plurality of sensors, cardiac health associated with at least one of an implanted device or a surgery.

46 Claims, 12 Drawing Sheets

(51) Int. Cl.
*A61B 5/145* (2006.01)
*A61F 2/24* (2006.01)
*A61B 5/0215* (2006.01)
*A61B 5/042* (2006.01)
*A61B 5/0428* (2006.01)
*A61B 5/0408* (2006.01)

(52) U.S. Cl.
CPC .......... *A61B 5/02158* (2013.01); *A61B 5/042* (2013.01); *A61B 5/0422* (2013.01); *A61B 5/04284* (2013.01); *A61B 5/14539* (2013.01); *A61B 5/14542* (2013.01); *A61F 2/24* (2013.01); *A61F 2/2427* (2013.01); *A61F 2/2478* (2013.01); *A61B 5/0408* (2013.01); *A61B 2560/0219* (2013.01); *A61B 2560/0271* (2013.01); *F04C 2270/041* (2013.01)

(58) Field of Classification Search
CPC .............. A61B 5/0422; A61B 5/04284; A61B 5/14539; A61B 5/14542; A61B 5/0408; A61B 2560/0219; A61B 2560/0271; A61B 17/07207; A61F 2/24; A61F 2/2427; A61F 2/2478
USPC .......................................................... 606/232
See application file for complete search history.

(56) References Cited

U.S. PATENT DOCUMENTS

| | | | |
|---|---|---|---|
| 4,995,857 | A | 2/1991 | Arnold |
| 5,817,133 | A * | 10/1998 | Houben ............... A61N 1/3704 607/9 |
| 5,987,352 | A * | 11/1999 | Klein ..................... A61N 1/375 600/509 |
| 6,409,674 | B1 | 6/2002 | Brockway et al. |
| 6,547,725 | B1 * | 4/2003 | Paolitto .............. A61B 17/0206 600/201 |
| 6,783,499 | B2 | 8/2004 | Schwartz |
| 6,855,115 | B2 | 2/2005 | Fonseca et al. |
| 6,926,670 | B2 | 8/2005 | Rich et al. |
| 6,969,369 | B2 | 11/2005 | Struble |
| 7,070,591 | B2 | 7/2006 | Adams et al. |
| 7,212,871 | B1 * | 5/2007 | Morgan ............... A61N 1/0587 607/129 |
| 7,409,244 | B2 | 8/2008 | Salo et al. |
| 7,416,530 | B2 | 8/2008 | Turner et al. |
| 7,425,200 | B2 | 9/2008 | Brockway et al. |
| 7,717,854 | B2 | 5/2010 | Mann et al. |
| 7,798,973 | B2 | 9/2010 | Stahmann |
| 7,801,608 | B2 | 9/2010 | Li et al. |
| 7,909,770 | B2 | 3/2011 | Stern et al. |
| 7,931,597 | B2 | 4/2011 | Bodecker et al. |
| 7,931,598 | B2 | 4/2011 | Bodecker et al. |
| 8,016,764 | B1 | 9/2011 | Shelchuk |
| 8,031,076 | B2 | 10/2011 | Sachanandani et al. |
| 8,075,491 | B2 | 12/2011 | Bharmi |
| 8,142,363 | B1 | 3/2012 | Eigler et al. |
| 8,147,416 | B2 | 4/2012 | Fayram et al. |
| 2002/0103521 | A1 * | 8/2002 | Swoyer ................... A61N 1/05 607/116 |
| 2002/0120200 | A1 | 8/2002 | Brockway et al. |
| 2005/0137672 | A1 * | 6/2005 | Coe ................... A61B 17/0469 607/126 |
| 2006/0149330 | A1 | 7/2006 | Mann et al. |
| 2007/0032734 | A1 | 2/2007 | Najafi et al. |
| 2007/0106358 | A1 * | 5/2007 | Westlund ............. A61N 1/0587 607/122 |
| 2008/0051850 | A1 * | 2/2008 | Sparks .................. A61F 5/0026 607/40 |
| 2008/0097383 | A1 * | 4/2008 | Vinten-Johansen A61M 25/0026 604/508 |
| 2009/0018606 | A1 * | 1/2009 | Sparks ................ A61N 1/0509 607/40 |
| 2009/0105557 | A1 | 4/2009 | Najafi et al. |
| 2009/0105605 | A1 | 4/2009 | Abreu |
| 2009/0276023 | A1 * | 11/2009 | Morris ................. A61N 1/0558 607/116 |
| 2010/0174201 | A1 | 7/2010 | Bodecker et al. |
| 2010/0249882 | A1 | 9/2010 | Houben |
| 2011/0046452 | A1 | 2/2011 | Najafi et al. |
| 2011/0124992 | A1 | 5/2011 | Brauker et al. |
| 2011/0230771 | A1 | 9/2011 | Koh et al. |
| 2011/0295363 | A1 * | 12/2011 | Girard .................. A61F 2/2412 623/1.26 |
| 2012/0022507 | A1 | 1/2012 | Najafi et al. |
| 2012/0108984 | A1 | 5/2012 | Bennett et al. |

OTHER PUBLICATIONS

International Search Report and Written Opinion dated Sep. 14, 2012 for PCT Application No. PCT/US1241582, filed Jun. 8, 2012.
Wireless, Batteryless Implantable Medical Products, © 2008 ISSYS Sensing Systems, Inc., Retrieved from the Internet: <URL:http://www.mems-issys.com/implantablc.shtml> (3 pages).

* cited by examiner

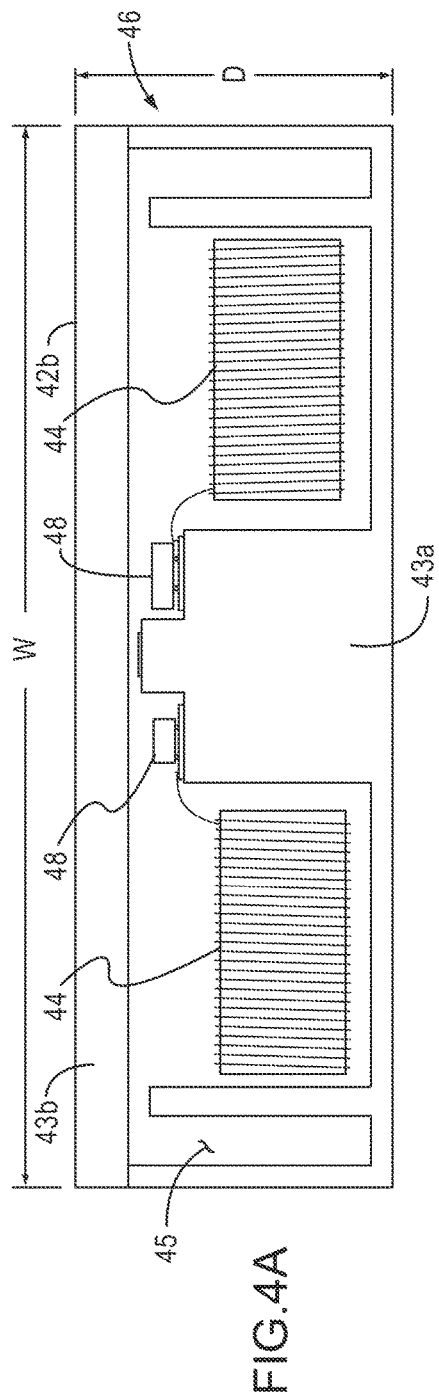
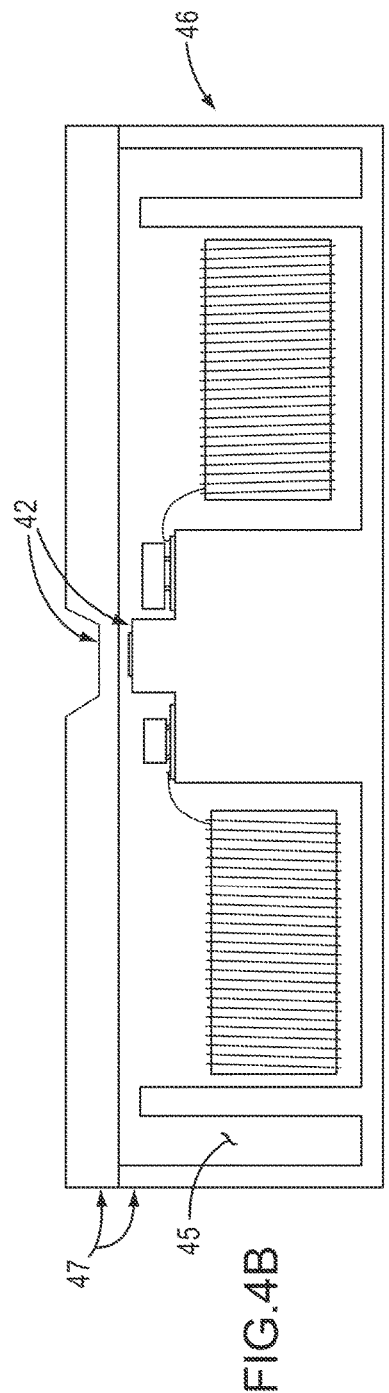
FIG.4A
FIG.4B

IMPLANTABLE WIRELESS SENSOR SYSTEMS

CROSS-REFERENCE TO RELATED APPLICATIONS

This non-provisional utility application claims priority to and the benefit of U.S. provisional application Ser. No. 61/494,536, filed on Jun. 8, 2011 entitled "Implantable Wireless Sensors as Companion Devices to Cardiac Operations", the disclosure of which is incorporated by reference herein in its entirety.

TECHNICAL FIELD

Some embodiments relate generally to implanted wireless sensors and sensor systems measuring one or more biomedical parameters for monitoring cardiac health.

BACKGROUND

Cardiac operations are increasingly commonplace, and usually necessary, given the critical contribution cardiac health makes to a person's well being and survival. It is also recognized, however, that the invasive nature of cardiac procedures, whether they involve implantation of a cardiac device such as a pacemaker or valve repair, has the potential to produce post-surgery stress responses. For example, arrhythmias following cardiothoracic surgery are thought to result from direct mechanical irritation of the pericardium or myocardium, and due to increased sympathetic and hormonal activity. In another example, the use of cardiopulmonary bypass is considered to be linked to systemic inflammatory responses.

Some known approaches to monitoring cardiac health after surgery use implanted cardiac sensors. Wired sensors, however, require passage of wires through cutaneous layers, thereby risking physical injury and infection. Wireless sensors are hence more desirable for such biological operation. Implantation of sensors, however, is an invasive procedure by itself, which elevates and contributes to the risk faced by the patient. There is hence a need for sensors and sensor systems that reduce or otherwise minimize the additional risk associated with sensor-based monitoring of cardiac health after surgery and/or after implantation of a cardiac device.

SUMMARY

In some embodiments, a cardiac monitoring system includes multiple sensors configured for implantation in a cardiovascular system of a user. Each sensor includes a sensing unit configured to be disposed in sensory communication with a location in the cardiovascular system for measuring a biological parameter in the location. The sensing unit is also configured to generate a sensory signal associated with the biological parameter. Each sensor also includes a wireless transceiver configured to receive the sensory signal from the sensing unit. The wireless transceiver is further configured to wirelessly transmit the sensory signal to an external processing device disposed outside a body of the user. The external processing device monitors, based on the sensory signal received from at least two sensors from the plurality of sensors, cardiac health associated with at least one of an implanted device or a surgery.

BRIEF DESCRIPTION OF THE DRAWINGS

FIG. 4A illustrates a flat sensing assembly, according to an embodiment;

FIG. 4B illustrates the flat sensing assembly of FIG. 4A in a deformed configuration;

DETAILED DESCRIPTION

Figure 1:
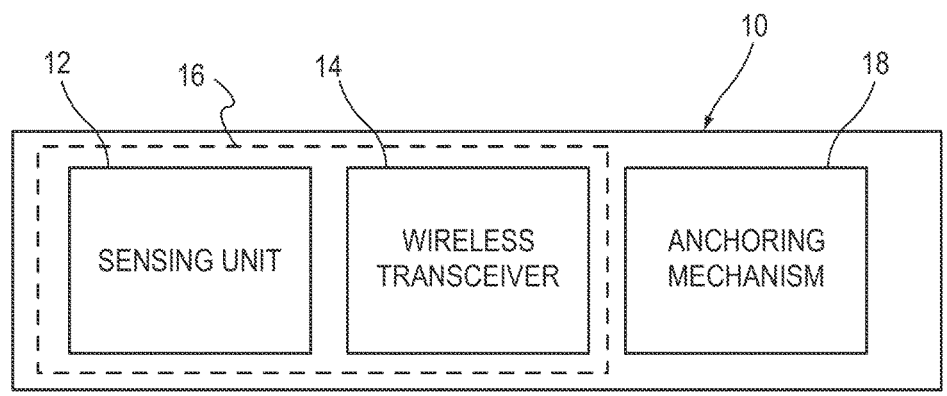
FIG. 1 is a schematic illustrating a sensor, according to an embodiment.

Sensors, cardiac monitoring systems, and methods of cardiac monitoring are disclosed herein. In some embodiments, a cardiac monitoring system includes multiple sensors that can be implanted in one or more locations in the cardiovascular system including, without limitation, a wall of at least one heart chamber of a user, a wall of an artery (e.g. the pulmonary artery), a wall of a vein, and/or the like. Similarly stated, one or more sensors can be implanted in any number of heart chambers. Each sensor can include a sensing unit in sensory communication with the heart chamber in which the sensing unit is implanted. The sensing unit can measure a biological parameter in the heart chamber. The sensing unit generates a sensory signal associated with the biological parameter, such as, for example, an electrical and/or magnetic signal in response to the biological parameter (e.g., pressure) sensed in the heart chamber. Each sensor can also include a wireless transceiver that can receive the sensory signal from the sensing unit and can wirelessly transmit the sensory signal to an external processing device. The external processing device can be disposed outside the body of the user, such that the wireless sensory signal is transmitted through the body of the user.

The external processing device can employ the wirelessly received sensory signal to monitor cardiac health. For example, the sensor can be a pressure sensor implanted in the left atrium of the user, and the external processing device can monitor the sensed pressure to determine whether the mitral valve formed between the left atrium and the left ventricle is functioning properly. Further, in some embodiments, the external processing device can monitor cardiac health based on multiple sensors (i.e., at least two sensors). For example, the sensors can be placed on either side of a repaired mitral valve, and the external processing device can monitor post-repair valve operation via the sensors. Further, the external processing device can monitor an implanted device based on the signal from the sensor(s). For example, the external processing device can be programmed to determine if an implanted left ventricular assist device (LVAD) is functioning properly based on pressure data obtained from two sensors, one implanted in the left atrium (LA) and the other implanted in either the right ventricle (RV), the left ventricle (LV) or the right atrium (RA). In this manner, the external processing device is capable of using the sensor data to monitor cardiac health due to an implanted device and/or a surgery.

In some embodiments, the implanted sensors do not directly communicate their sensory signals to other sensors. Similarly stated, even though the implanted sensors can be mechanically, electrically or functionally linked, the sensory signals are not directly exchanged. In some embodiments, at least one implanted sensor directly communicates a sensory signal to at least one other sensor. It is also possible that the implanted sensors do not directly communicate their sensory signals to the implanted device, which can be otherwise linked to one or more sensors. The implanted device can be in communication with one or more sensors and/or with the external processing device. In some embodiments, at least part of the function of the external processing device can be integrated into the implantable device.

In some embodiments, the wireless transceiver and the sensing unit are coupled, combined and/or bonded together to form a sensing assembly, which can further include a housing. The sensing assembly can be provided in various shapes and configurations, including, but not limited to, cylindrical, flat, and multipart sensing assemblies. Each different sensing assembly design provides different structural characteristics, and hence it is possible to choose a sensing assembly design for implantation based on the nature of the implantation site. For example, a cylindrical sensing assembly can be preferably employed when the wall of the implantation site is relatively thick, while a multipart sensing assembly can be employed when the implantation site provides spatial constraints and cannot accommodate all sensor components. The term 'implantation site' as used herein with respect to a sensor, a sensing device, and/or an implanted device generally means the site where the sensor, sensing device, and/or the implanted device, respectively is intended to be implanted.

It is understood that the shape of the sensing assembly and/or the housing of the sensing assembly can be used to characterize the sensor as well. Similarly stated, a cylindrical sensor would have a cylindrical sensing assembly, a flat sensor would have a flat sensing assembly, a multipart sensor would have a multipart sensing assembly, and so on.

In some embodiments, micro electromechanical systems (MEMS) technology can be used to form and/or manufacture the sensing unit and/or the sensing assembly including, for example, bulk micromachining, surface micromachining, dissolved wafer process, high aspect ratio micromachining, nanotechnology, and/or the like.

The anchoring mechanism can be a hollow cylindrical anchor holding the sensor components and/or the housing containing the sensing assembly, and can have a length that is selected based on the nature of the implantation site (e.g. a known wall thickness of the implantation site). The cylindrical anchor can include, for example, a button portion that is broader than the diameter of the implantation site of the sensor. In this manner, the cylindrical anchor can serve as a 'plug' that also seals the implantation site. For example, if the implantation site was created during surgery (e.g., the implantation site is a surgical site necessary for the surgery) and needs to be sealed after surgery, the cylindrical sensor can perform a sealing function as well by virtue of its design.

The term 'surgical site' as used herein with respect to an implanted device generally means a site that was used during the implantation of the implanted device, but does not hold the implanted device. Stated similarly, for an implanted device, the surgical site is different from the implantation site (described above) of the implanted device. For example, a cavity, aperture or hole defined during implantation of the implanted device can be considered a surgical site. The term 'surgical site' as used herein with respect to a surgery, means any site (e.g., portion of the body) used for the purposes of performing the surgery. In some embodiments, the surgical site(s) can serve as implantation site(s) for the sensors described herein. In some embodiments, the sensor can pass through a surgical sites for implantation in a different site. For example, a cavity, aperture or hole defined during a surgery can be considered a surgical site.

In some embodiments, relatively flat sensing assemblies can be used when a low profile of the sensor is desirable. A sensing assembly can be generally characterized as 'flat' when its dimension along the depth of the implantation site is smaller than its dimension along a surface of the implantation site. For example, a cylindrical sensing assembly that has a thickness smaller than its width can be characterized as a flat sensing assembly, since it has a low depth of implantation.

In some embodiments, multipart sensing assemblies can separate the sensing unit and the wireless transceiver into two or more subassemblies. A first subassembly, for example, can be a sensing subassembly that includes at least the sensing unit, while one or more of the other components are disposed in a non-sensing subassembly. For example, the sensing subassembly can include the sensing unit and can optionally include processing electronics, while the non-sensing subassembly can include relatively bulkier components such as an induction coil of the wireless transceiver, electronics, and/or power components. In some embodiments, the sensing subassembly provides a smaller footprint and/or is smaller relative to the non-sensing subassembly, in terms of surface area, a dimension, shape, and/or volume. In some embodiments, the sensing subassembly can be implanted in a heart chamber, while the non-sensing assembly can be disposed elsewhere, for example, in another organ, a natural cavity of the patient's body, another portion of the patient's body, or outside the patient's body. The subassemblies can be tethered together electrically, mechanically, and/or by any other suitable means.

While discussed above for pressure, any suitable biological parameter, and/or any number of parameters, can be sensed by each sensing unit including, for example, blood pressure, temperature, blood pH, conductivity, one or more dielectric constants, chemical concentration, a gas content (e.g. oxygen), a metabolite (e.g. glucose), and/or the like.

In some embodiments, the sensing unit can be designed as a capacitive sensing unit. Similarly stated, the sensing unit can operate on the general principle that variation in distances between two electrodes, such as under the influence of a biological parameter, translates to a change in capacitance, where a measure of the change in capacitance is associated with a measure of the biological parameter affecting the change. In some embodiments, at least one electrode is rigidly attached to a substrate, while the other electrode is flexibly attached to the substrate. Flexible attachment permits limited movement of the flexible electrode, and hence results in variation in capacitance as described above.

In some embodiments, one or more of the implanted sensors receives power from an external power source and/or device for operation. Hence, the externally-powered implanted sensor(s) need not include a power source, and alternatively can have a power storage device (e.g. a rechargeable battery, a capacitor, and/or the like) that stores the received power. In some embodiments, the external processing device can provide the external source of power. Similarly stated, the external processing device and the external power source can be collocated. In some embodiments, the wireless transceiver of the sensor can have a single coil for both sensory and power telecommunication. In other embodiments, the wireless transceiver can include a first coil for sensory telecommunication and a second coil for power telecommunication. In some embodiments, the power and/or sensory signals are transmitted by the wireless transceivers via wireless telemetry.

The external processing device can include a readout unit for interfacing the external processing device, such as a display, a Universal Serial Bus (USB) port, a printer, a speaker, and/or any other suitable presentation device. The readout unit can also include signal conditioning, control and/or analysis circuitry and software, can be a stand alone unit or can be connected to a personal computer (PC) or other computer controlled device. The external processing device can monitor the implanted sensors, power the implanted sensors, and/or control the operation of the implanted sensors. The external processing device can additionally or alternatively wirelessly monitor the implanted device, and/or wirelessly control the implanted device.

The implanted device can be any device implanted in the heart, such as a ventricular assist device (VAD) or a replacement valve. Further, in embodiments where the external processing device monitors cardiac health associated with a surgery, any suitable surgery is envisioned, including, for example, a coronary artery bypass graft (CABG), a valve repair, a transcatheter aortic valve operation, a catheter-based operation, a minimally invasive surgery and/or the like.

In some embodiments, a method includes measuring a first biological parameter at a first sensor implanted in a wall of a first chamber of a heart of a user, and generating a first sensory signal associated with the first biological parameter. The method also includes wirelessly transmitting, by the first sensor, the first sensory signal to an external processing device located outside the body of the user. The method also includes measuring a second biological parameter at a second sensor implanted in a wall of a second chamber of the heart, and generating a second sensory signal associated with the second biological parameter. The first and second biological parameters can be suitably selected. In some embodiments, the first and second biological parameters are the same parameter. In other embodiments, the first and second biological parameters are different parameters. The method further includes wirelessly transmitting, by the second sensor, the second sensory signal to the external processing device. The method additionally includes monitoring, based on at least one of the first sensory signal or the second sensory signal, cardiac health associated with at least one of an implanted device or a surgery. Similarly stated, the method provides for cardiac monitoring of a biological parameter after surgery and/or an implanted device via at least two sensors implanted in the heart.

In some embodiments, sensory signals are not communicated between the sensors and/or between the sensors and the implanted device. In other embodiments, sensory signals can be transmitted between the sensors and/or the sensors and an implanted device.

The sensing assemblies of the sensors can be independently designed as cylindrical, flat, and/or multipart assembly, and can be further suitably selected depending on the implantation site, as described above. The sensing unit of at least one of the first and second sensor can be capacitive, and can include a flexible electrode attached to a substrate. In some embodiments, at least one of the first sensor or the second sensor includes additional component(s) such as, for example, a battery, a capacitor, a super capacitor, and/or any other suitable power storage device.

The method can further include monitoring, at the external processing device, sensing information (first and/or second sensory signal), the implanted device, and/or cardiac health. For example, the external processing device can be operable to receive, transmit, and/or otherwise manipulate data associated with any of these monitored features. For example, the external processing device can monitor, charge, and/or control any of the sensors, and can further monitor, charge, and/or control the implanted cardiac device.

The method can also include implanting additional sensors, such as a third sensor, in the heart of the patient. In some embodiments, the method includes placing at least one sensor via a placement catheter. In some embodiments, the sensors are implanted during the same procedure employed for implanting the cardiac device, and/or during a surgery. This can reduce the risk of additional surgical exposure to the patient. When the surgery and/or device implantation results in a surgical site or 'hole' in the heart of the patient, at least one of the sensors can be implanted in the surgical site or hole. In this manner, the surgical site is substantially sealed and an additional implantation site for at least one sensor is not required. Further, when the sensor is placed in the surgical site, the sensor can be suitably selected (e.g. as having a cylindrical, flat, or multipart sensing assembly) based on the nature of the surgical site, as described above.

In some embodiments, the sensor is configured to achieve occlusion by a sealing fit and retention of the sensor in its implantation site. In other words, the sensor, or any portion thereof, can be sized, formed of a material, coated, covered, or otherwise treated to increase frictional contact between the surface or surfaces contacting the sensor, and the sensor. The sensor or portions thereof can, for example, be textured, by hatching the surfaces of the sensor. In another example, the sensor can be partly or coated with a slip resistant and biocompatible coating, such as, for example, a viscous gel. In some embodiments, the frictional contact can be increased by the use of a compliant covering. The compliant covering may deform upon pressure contact with the implantation site, which increases the surface area of interaction between the compliant covering and the implantation site, which in turn increases friction. An additional or alternative approach to increasing friction is the use of adhesive materials, and/or coverings. In other embodiments, and as described in further detail herein, any other suitable anchoring method and/or device can be used, such as, for example, sutures, mesh, and/or the like.

In some embodiments, a method includes implanting in a patient a circulatory assist device, such as a VAD or a replacement valve. The method also includes implanting, in a wall of a first chamber of a heart of the patient, a first sensing device in sensory communication with the first chamber of the heart. The first sensing device is operable to measure a first biological parameter in the first chamber of the heart relevant to a performance of the circulatory assist device. The first sensing device is also operable to wirelessly transmit a first signal representative of the first biological parameter to an external processing device disposed outside a body of the patient. The method also includes implanting, in a wall of a second chamber of the heart of the patient, a second sensing device in sensory communication with the second chamber of the heart. The first and second sensing devices can be, for example, pressure sensors. The second sensing device is operable to measure a second biological parameter in the second chamber of the heart relative to the performance of the circulatory assist device. The first and second biological parameters can be the same or different. The second sensing device is also operable to wirelessly transmit a second signal representative of the second biological parameter to the external processing device. The method further includes placing the external processing device into operative wireless communication with each of the first sensing device and the second sensing device. In some embodiments, the external processing device can monitor operation of the circulatory assist device based on the first signal and the second signal.

In some embodiments, the first and/or second sensing device(s) is/are implanted during implantation of a circulatory assist device, thereby avoiding additional risk and trauma to the patient caused by additional surgical procedures. In some embodiments, the method includes implanting the first sensing device in a surgical site (e.g., aperture and/or hole) formed during implantation of the circulatory assist device such that there is no need for a separate implantation site for the first sensing device. The sensing devices can be charged, monitored, and/or controlled by the external processing device, which can also charge, monitor, and/or control the circulatory assist device.

A sensor 10 according to an embodiment is schematically illustrated in FIG. 1. The sensor 10 includes a sensing unit 12, a wireless transceiver 14, and an anchoring mechanism 18. Optionally, the sensing unit 12 and the wireless transceiver 14 can be combined, attached, or bonded together in a housing 16 to form a sensing assembly (also indicated by reference character 16) prior to attachment to the anchoring mechanism 18 to define the sensor 10.

The sensing unit 12 is configured to be disposed, when the sensor 10 is implanted in a wall of a heart chamber, to be in sensory communication with the heart chamber for measuring a biological parameter in the heart chamber, and is further configured to generate a sensory signal associated with the biological parameter. In some embodiments, the biological parameter can be, for example, blood pressure, temperature, blood pH, conductivity, a dielectric constant, a chemical concentration, a gas content (e.g. oxygen), a metabolite (e.g. glucose), and/or the like. In some embodiments, the sensing unit 12 can be configured to measure more than a single biological parameter.

In some embodiments, the cardiovascular system can include, without limitation, a heart chamber that can include, for example, the left atrium (LA), the right atrium (RA), the left ventricle (LV), the right ventricle (RV), the left atrium appendage (LAA), the right atrium appendage (RAA), or veins, or arteries such as a pulmonary artery (PA) and/or the like. In some embodiments, the wall of the heart chambers can include, for example, a wall of the LA, a wall of the RA, a wall of the LV, a wall of the RV, an interatrial septum, an interventricular septum, an atrioventricular septum and/or the like. In some embodiments, the sensing unit 12 can be configured to measure more than one biological parameter, and can be further configured to generate a separate sensory signal for each measured biological parameter.

In some embodiments, the sensing unit 12 is a capacitive sensing unit having two electrodes and based on the general concept that when a small deformable membrane forms or contains one electrode of a capacitor and moves towards or away from the other electrode in response to pressure, a variation in capacitance is observed. In some embodiments, the capacitive sensing unit consists of one flexible electrode and one stationary electrode. In some embodiments, the stationary electrode can be formed, for example, on a substrate, and the flexible electrode can be attached to the same substrate or a separate substrate, such that there is a gap between the two electrodes. The flexible electrode can be configured to move in response to the biological parameter, for example, blood pressure in a heart chamber. Movement of the flexible electrode changes the gap between the two electrodes and thus the capacitance, which can be used to calculate pressure changes. In some embodiments, at least one of the substrates forms the electrode. Similarly stated, the substrate and the electrode can be integrally formed. The electrodes of the sensing unit 12 can be physically and/or communicatively coupled to other components of the sensor 10 using suitable mechanical and/or electrical means, including, but not limited to, signal traces, wires, and/or the like.

Still referring to the substrates of the sensing unit 12, in some embodiments, the substrates on which the electrodes are formed or fabricated can be either rigid, partly rigid and partly flexible (rigiflex substrates), or flexible. Rigid components of substrates can be composed of any suitable material, such as, for example, glass, silicon, ceramics, carbides, alloys, metals, hard polymers, and Teflon and/or the like: Flexible components of substrates can be composed of any suitable material, such as, for example, polymers, parylene, silicone, and/or any biocompatible flexible material. In some embodiments, at least one of the substrates is a rigiflex substrate, and the rigid and flexible components can be made from dissimilar materials. In some embodiments, the material of the substrates increases frictional contact (i.e., by increasing the frictional coefficient) between the substrate and the implantation site.

Still referring to the sensor 10 of FIG. 1, the wireless transceiver 14 of sensor 10 is configured to receive the sensory signal from the sensing unit 12. In some embodiments, the wireless transceiver 14 directly receives the sensory signal from the sensing unit without any manipulation of the sensory signal output of the sensing unit 12. In other embodiments, the wireless transceiver 14 receives the sensory signal after signal processing by one or more intermediate components (e.g., an amplifier, a rectifier, a DC-to-AC converter, an AC-to-DC converter, an application specific integrated circuit (ASIC), a processing device and/or the like) disposed between the sensing unit 12 and the wireless transceiver 14. The sensory signal received by the wireless transceiver may be in any suitable format, for example, analog, digital, and/or the like. The sensory signal may further include any suitable information about the monitored biological parameter, including, for example, the absolute value of the parameter, a statistical value of the parameter (e.g. average, moving average, deviation, and/or the like), the value of an electrical current and/or voltage generated by variations in the parameter, and/or the like.

The wireless transceiver 14 is further configured to wirelessly transmit the received sensory signal. In some embodiments, the wireless transceiver 14 transmits the sensory signal without modification. In other embodiments, the wireless transceiver 14 processes the sensory signal prior to transmission by, for example, amplification, rectification, frequency conversion, modulation, format conversion (e.g., binary to hexadecimal), data manipulation (e.g., adding an identification of the sensor 10 to the received sensory signal), and/or the like.

In some embodiments, the wireless transceiver 14 employs one or more modulation schemes for transmitting the sensory signal data. The modulation scheme(s) can be, for example, amplitude modulation, frequency modulation, frequency shift keying, phase shift keying, spread spectrum techniques, and/or the like. In some embodiments, the modulation scheme is selected as a function of the intended use of the sensor 10, the depth of implantation of the sensor, the location of implantation of the sensor, and/or the like.

In some embodiments, the wireless transceiver 14 is also operable to receive a power signal for powering the sensor 10. In some embodiments, the wireless transceiver 14 includes an inductor coil and a core. In some embodiments, the core includes a ferrite composition. In other embodiments, the core is an air core. In some embodiments, the sensor 10 includes a power storage device (not shown), and the wireless transceiver 14 is coupled to the power storage device for storing the power received from the wireless transceiver. In some embodiments, the power storage device can include, for example, a rechargeable battery, a capacitor, a super capacitor, and/or any other suitable power storage device.

Still referring to the wireless transceiver 14, in some embodiments, an inductor coil of the wireless transceiver 14 is made by deposition of a conductive coil on a substrate. In some embodiments, the deposition process includes one or more of electroplating, sputtering, evaporation, screen printing, and/or the like. In some embodiments, the conductive coil is made from one or more highly conductive metals such as silver, copper, gold, and combinations thereof. In some embodiments, the substrate of the induction coil can be rigid, flexible, or partly rigid and partly flexible. In some embodiments, the inductor coil is of a shorter length compared to its width and is hence relatively flat (e.g., coin shaped). In some embodiments, the length of the inductor coil is the same as or larger than its width, such that the inductor coil is thicker and takes on a three-dimensional profile such as, for example, a cylinder.

In some embodiments, the wireless transceiver 14 transmits the sensory signal, receives the power signal, and/or otherwise communicates with other devices based on magnetic telemetry, i.e., via magnetic coupling. In some embodiments, magnetic coupling occurs via an externally applied RF magnetic field. In some embodiments, a single induction coil of the wireless transceiver 14 performs the dual task of transmitting the sensory signal and receiving the power signal. In other embodiments, the wireless transceiver 14 includes two induction coils, where a first induction coil transmits the sensory signal and a second induction coil receives the power signal. In some embodiments, the wireless transceiver 14 is operable to rectify the incoming power waveform to define a direct current.

Referring now to the anchoring mechanism 18 illustrated in FIG. 1, the anchoring mechanism is configured to hold, attach, fix, retain and/or otherwise anchor the sensor 10 to a wall of a heart chamber. In some embodiments, the anchoring mechanism 18 attaches to at least one of the sensing unit 12, the wireless transceiver 14, and/or the sensing assembly 16. In some embodiments, for example, the design of the anchoring mechanism 18 can be selected based on the implantation site. The anchoring mechanism 18 can be integral to the sensor 10, or can be separately formed and attached during assembly. In some embodiments, the anchoring mechanism 18 can include wires, screws, bolts, meshes, stents, springs, stitches, expanding tines, and/or the like. In some embodiments, an additional material, such as felt, can also be placed between the anchoring mechanism 18 and the implantation site. In some embodiments, the anchoring mechanism 18 is configured to attach and/or tether the sensor 10 to an implanted device, for example, a pacemaker, a VAD and/or the like. In some embodiments, the anchoring mechanism 18 is integral to, unitarily formed with, and/or part of the implanted device.

Any suitable biocompatible material can be used for constructing the anchoring mechanism 18, including, for example, nitinol, teflon, parylene, Polyether ether ketone (PEEK), suitable polymers, metals, ceramics, and/or the like.

Referring again to the sensor 10 in FIG. 1, in some embodiments, the sensor further includes electronic circuitry coupled to the wireless transceiver 14 such as one or more application specific integrated circuits (ASICs), one or more processing devices, one or more capacitors, and/or one or more diodes, for performing the sensor's function.

In some embodiments, a biocompatible coating covers part or all of the sensor 10. In some embodiments, the biocompatible coating does not cover the portion of the sensing unit 12 that interacts with the biological environment (e.g. a flexible electrode, as discussed above). Such a biocompatible coating can be, for example, a silicone, a hydrogel, parylene, a polymer, a nitride, a oxide, a nitric oxide generating material, a carbide, a silicide, titanium, and/or the like. In some embodiments, the biocompatible coating increases friction between the sensor 10 and the implantation site.

In some embodiments, additional components can be formed as part of sensor 10, such as, for example, a power storage device (e.g. a battery, capacitor, and/or the like), getters, and/or the like. Suitable materials for getters includes, for example, evaporable getters, nanogetters, titanium films, zirconium films, iron films, and/or the like.

Figure 2:
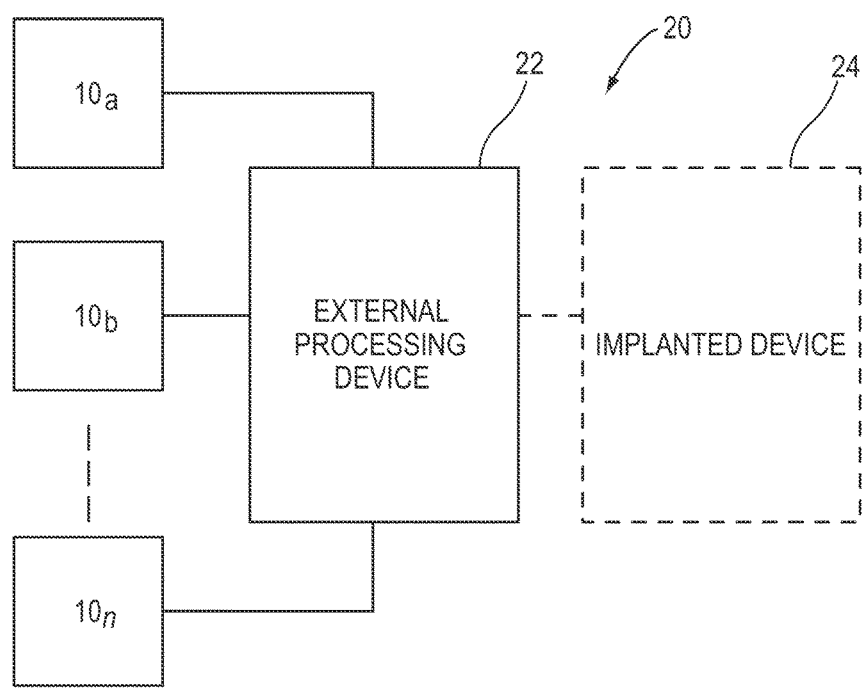
FIG. 2 is a schematic illustrating a cardiac monitoring system, according to an embodiment.

Referring now to FIG. 2, a cardiac monitoring system 20 according to an embodiment is generally illustrated. The system 20 includes sensors 10a-10n, an external processing device 22, and optionally, an implanted device 24, such as pacemakers, defibrillators, VAD's, etc. While shown and described with respect to FIG. 2 as having an implanted device 24, in other embodiments, the cardiac monitoring system 20 does not include an implanted device, or includes an implanted device but is not structurally and/or functionally linked with the implanted device (where the dotted line connecting the external processing device 22 and the implanted device 24, as well as the implanted device 24, are each illustrated with dotted lines as optional) and sensors 10a-10n are implanted to monitor one or more biological parameters after a surgical procedure. Unless stated otherwise, it is understood that each sensor 10a-10n is structurally and/or substantially similar to the sensor 10 of FIG. 1.

The subscript 'n' is used to indicate that one or more sensors are part of the system 20. In some embodiments, for example, n is one. In other embodiments, n can be any other suitable number, for example, two, three, four, or five. In still other embodiments, n can be greater than five.

The external processing device 22 of system 20 is configured to receive sensory signals from the sensors 10a-10n, and based on the sensory signals received from at least one or more sensors (e.g. two sensors, in some embodiments), monitor cardiac health associated with the implanted device 24 and/or a surgical procedure. In some embodiments, the device 22 also controls the sensors 10a-10n (e.g., instruct the sensors 10a-10n to measure a biological parameter at a given rate, request the sensors 10a-10n to measure a biological parameter on-demand, provide power to the sensors 10a-10n, change the biological parameter measured by the sensor, etc.).

In some embodiments, the device 22 wirelessly powers the sensors 10a-10n. In some embodiments, communication of data and/or power between the device 22 and sensors 10a-10n is based on RF magnetic telemetry. In some embodiments, the device 22 is operable when brought within a suitable range and/or operative proximity of the sensors 10a-10n. The device 22, for example, can establish magnetic and/or inductive coupling with the sensors 10a-10n via an RF magnetic field. In some embodiments, the device 22 transmits a substantially continuous level of RF power to sensors 10a-10n. In other embodiments, for example, the device 22 pulses the magnetic RF power to the sensors 10a-10n, to allow temporary power storage by the sensor in, for example, a power storage device (not shown).

When the magnetic field is large enough to induce sufficient voltage in the wireless transceiver 14 of a particular sensor 10, the sensor can be considered 'active' to transmit sensory signals to the device 22, and/or to respond to control signals from the device 22. In some embodiments, the device 22 receives sensory signals from the sensors 10a-10n at any suitable interval of time that is preprogrammed and/or otherwise communicated to the sensors. The received sensory signals can be instantaneous or time-delayed. In some embodiments, device 20 receives, or otherwise programs the sensors 10a-10n to transmit the sensory signals during power transmission by device 22, or before/after power transmission by device 22. In some embodiments, the device 22 has at least two modes of operation: a data logging measurement mode with relatively lower rates of sensory signals being received (e.g. about 1 Hz), and a real-time dynamic measurement mode with relatively higher rates of sensor signals being received (e.g. about 100-500 Hz, and all values in-between). In some embodiments, the sensory signals are transmitted using the 13.56 MHz industrial, scientific and medical (ISM) radio band as currently defined by the International Telecommunication Unions (ITU). In other embodiments, the sensory signals are transmitted at any other suitable frequency, as specified by the prevailing regulatory authority and/or standard.

In some embodiments, the external processing device 22 includes an antenna (not shown) and/or a readout unit (not shown). In some embodiments, the readout unit of device 22 includes an analog RF front end, a receiver and/or demodulator, a digital processor, and/or a programmable user interface. Such components of the readout unit can be used by the external processing device 22 to receive signals from and/or transmit signals to the sensors 10a-10n and/or the implanted device 24.

In some embodiments, the external processing device 22 is disposed within a body of a user but outside a heart of the user. In other embodiments, the external processing device 22 is disposed outside the body of the user. A location of the external processing device 22 can be selected based on a size of the external processing device 22, a functionality of the external processing device 22, a parameter to be monitored, and/or the like.

Now referring to the entirety of the system 20 in FIG. 2, in some embodiments, the system is operable to monitor cardiac health during or after a surgery and/or a surgical procedure, where the surgery/surgical procedure may or may not result in the implantation of a device. The surgery can include without limitation, for example, transapical aortic valve implantation (TAVI), mitral valve repair surgery (which can include implantation of Mitraclip), implantation of ventricular assist devices (including, for example, left ventricular assist devices LVADs, right ventricular assist devices RVADs, and bi-ventricular assist devices BiVADs), extracorporeal membrane oxygenation (ECMO), coronary artery bypass graft (CABG) surgery, aortic valve replacement (AVR) or aortic prosthesis surgery, atrial fibrillation ablation, implantable cardioverter defibrillator (ICD) surgery, cardiac resynchronization therapy (CRT) or biventricular pacing, percutaneous transvenous mitral valvuloplasty (PTMV), surgeries for correction of congenital heart defects, pre and post heart transplant operations, implantation of pacemakers, implantation of defibrillators, and/or the like.

Referring to the implanted device 24 of FIG. 2, in some embodiments, the implanted device can be, for example, a transapical aortic valve, a replacement mitral valve, a left ventricular assist device (e.g., LVAD, RVAD, or BiVAD), a replacement aortic valve, an aortic prosthesis, a defibrillator (e.g. a cardioverter defibrillator), an implant for biventricular pacing, a pacemaker, and/or the like.

In some embodiments, the system 20 is a closed loop control system for the implanted device 24. Similarly stated, the implanted device 24 affects the biological parameter(s) monitored by the external processing device 22 via the sensors 10a-10n, and the processing device 22 can use this monitored information to control the implanted device 24. For example, based on one or more values of biological parameters received from the sensors 10a-10n, the external processing device 22 can send a signal to the implanted device 24 to change an operation of the implanted device 24 (e.g., a pump speed, an amount of a drug delivered, an interval of an electric pulse, etc.). In other embodiments, based on one or more values of biological parameters received from the sensors 10a-10n, a user's medication can be tailored, exercises for the user can be tailored and/or a user can make life style changes. In some embodiments, the system 20 is a substantially continuous and near real-time adjustment system, in which the external processing device 22 can send signals to the implanted device 24 without any programmed or built-in delay. In some embodiments, the system 20 is an intermittent adjustment system, in which the external processing device 22 can send signals to the implanted device 24 on a periodic basis that may be determined in any suitable manner (e.g., preprogrammed, based on signals received from the sensors 10a-10n, and/or the like). In some embodiments, the system 20 provides a manual adjustment system, in which the external processing device 22 receives manual commands (e.g., from a physician) to send signals to the implanted device 24.

In some embodiments, the system 20 is operable to perform, for example, remote (e.g. home) monitoring of patients, telephony-based monitoring of patients, web-based monitoring of patients, closed-loop drug delivery to treat the associated diseases or related conditions when the implanted device 24 is configurable for drug delivery, warning systems for critical worsening of the associated diseases (e.g., hydrocephalus or pulmonary edema) or related conditions, portable or ambulatory monitoring or diagnostic systems, battery-operation capability, data storage, reporting global positioning coordinates for emergency applications, and/or communication with other medical devices including but not limited to shunts, pacemakers, defibrillators including implantable cardioverter defibrillators, implantable drug delivery systems, non-implantable drug delivery systems, and wireless medical management systems.

Now describing the various components of FIG. 1 with additional detail, it should be understood that unless stated otherwise, similarly named components are structurally and/ or functionally similar to those shown and described with respect to FIG. 1. For example, the cylindrical sensing assembly 36 of FIG. 3 corresponds structurally and/or functionally to the sensing assembly 16 of FIG. 1.

Figure 3:
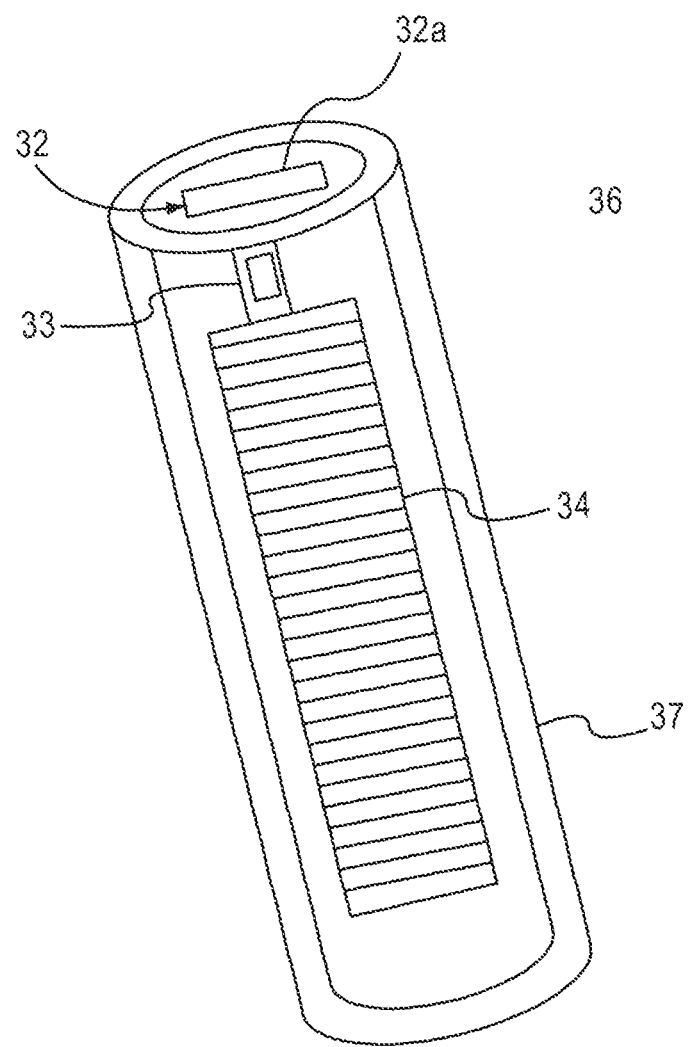
FIG. 3 illustrates a cylindrical sensing assembly, according to an embodiment.

FIG. 3 illustrates a cylindrical sensing assembly 36 with a capacitive sensing unit 32 formed on one end and having one flexible electrode 32a for interacting with a biological environment. The cylindrical assembly 36 also includes a wireless transceiver formed as an inductor coil 34. A connector and/or other electronics (collectively reference character 33) are formed between the sensing unit 32 and the coil 34, and can include, for example, a rectifier, an amplifier, a processing device (e.g., an ASIC) and/or the like. The cylindrical assembly 36 further includes a housing 37 that serves to hold together, enclose and/or retain the sensing unit 32 and the coil 34. In some embodiments, the housing 37 provides a hermetic seal that selectively prevents exposure of portions of the sensing unit 32 and/or the coil 34 to the biological environment. For example, the housing 37 may permit one capacitive electrode of the sensing unit 32 to interface a heart chamber, but otherwise prevent exposure of the second capacitive electrode of the sensing unit and the coil 34. Alternatively, in other embodiments, the various components of the sensor 30 can be potted together, such that the housing 37 is not used, yet a hermetic seal providing the protection described above can be achieved.

As described above, in use, the cylindrical sensing assembly 36 can be implanted in one or more sites within a body of a patient. For example, the cylindrical sensing assembly 36 can be implanted in a wall of a heart of a patient after combining the cylindrical sensing assembly with an anchoring mechanism. As described above, after implantation, the inductor coil 34 can be used to send signals to and/or receive signals from (e.g., power signals and/or data signals) an external processing device, such as, for example, external processing device 22 shown and described with respect to FIG. 2.

FIGS. 4A-4B illustrate a cross-section view of a round, flat sensing assembly 46 having a depth D less than a width W. Flat sensing assembly 46 can be of any suitable shape other than round, including, for example, rectangular, square, oval, and/or the like. The sensing unit 42 includes a fixed metal electrode 42a on a rigid (e.g., glass) substrate 43a, while the flexible electrode 42b is formed on a flexible substrate 43b. The flexible substrate 43b can be attached or otherwise bonded to the rigid substrate 43a. In this exemplary embodiment, and as illustrated in FIGS. 4A-4B, the rigid substrate 43a also provides attachment support for the components, other than the flexible electrode 42b, by means of cavities formed on the rigid substrate 42a. The cavities can be formed by any suitable means, such as, for example, etching, milling, machining, drilling, and/or the like. While FIGS. 4A-4B illustrate only substrate 43a as having cavities, in other embodiments (not shown), both substrate 43a and substrate 43b can be machined to some extent in order to accommodate the various components of the sensor assembly 46.

The components of the flat sensing assembly 46 include an induction coil 44 as a wireless transceiver, and additional electronics 48 (e.g., an amplifier, a rectifier, an ASIC, etc.). While shown as having a single induction coil 44, in other embodiments, the flat sensing assembly 46 can include more than a single induction coil or other antennas. The substrate 43a can also include, in a cavity 45, additional components such as, for example, a battery, a power storage device, and/or getters.

In some embodiments, the flat sensing assembly 46 can be manufactured by, for example, inserting and attaching the components to the rigid substrate 43a, followed by attaching the flexible substrate 43b to the rigid substrate. In some embodiments, this attachment not only results in realizing the capacitive sensing capability of the assembly 40, but also provides a hermetic seal that protects the various components from the biological environment. Similarly stated, the substrates 43a, 43b can combine to form a protective housing 47 for the flat sensing assembly 46. In some embodiments, the attachment method for the substrates 43a, 43b depends on the materials of the substrates to ensure that the attachment method does not damage the internal components. For example, if the rigid substrate 43a is made of glass and the flexible substrate 43b is made from silicon, permissible methods can include, for example, fusion bonding, anodic bonding, glass frit bonding, thermal bonding, thermal compression bonding, eutectic bonding, solder bonding, laser bonding, plasma-enhanced and/or low temperature variations of the aforementioned bonding methods, and/or the like.

Figure 5:
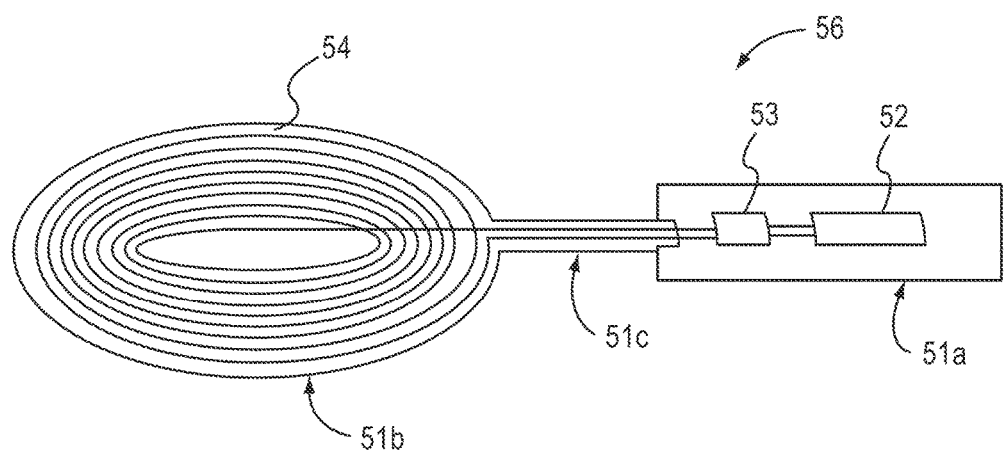
FIG. 5 illustrates a multipart sensing assembly, according to an embodiment.

FIG. 5 illustrates a multipart sensing assembly 56 having a sensing subassembly 51a and a non-sensing subassembly 51b joined together by a tether 51c. An anchoring mechanism, such as that described above with respect to FIG. 1, can be used with either or both subassemblies 51a, 51b. In the illustrated embodiment, the sensing subassembly 51a includes the sensing unit 52, while the non-sensing subassembly 51b includes the wireless transceiver formed as an inductive coil 54. In some embodiments, the non-sensing assembly 51b is larger or otherwise bulkier than the sensing assembly 51a, and is more favorably located outside the heart and/or body of the user.

In some embodiments, electronics 53 (e.g., an ASIC, a rectifier, an amplifier, one or more diodes, etc.) are included as part of the sensing assembly 51a in close proximity with sensing unit 52, and are configurable to convert the sensing unit's high impedance output to a low impedance output for ease of transfer to the non-sensing assembly for wireless transmission. In some embodiments, the electronics 53 and the sensing unit 52 are fabricated on the same substrate, fabricated separately but attached to the same substrate, or the sensing unit 52 includes a substrate and the electronics 53 are mounted directly on the sensing unit's substrate. In some embodiments (not shown), the electronics 53 are included as part of the non-sensing assembly 51b and are configurable for receiving, processing, and/or transmitting the signal received from the sensing assembly 51a.

In some embodiments, the tether 51c is an electrical and/or a mechanical connection. In some embodiments, the tether 51c is a flexible connection, a rigid connection, or a combination of flexible and rigid connections. In some embodiments, at least one of the subassemblies 51a, 51b and the tether 51c is coated, potted, or otherwise covered with a biocompatible coating, for purposes of, for example, increasing frictional contact of each component with its respective implantation or placement site.

As described above, in use, the multipart sensing assembly 56 can be implanted in one or more sites within a body of a patient. For example, sensing subassembly 51a can be implanted within a heart of a patient and the non-sensing subassembly 51b can be implanted within another portion of the body of the patient (e.g., a cavity). After implantation, sensing unit 52 can sense a value of a biological parameter. The value can be sent to the non-sensing subassembly 51b via the electronics 53 and the tether 51c. The inductive coil 54 can then send signal a signal associated with the value of the biological parameter to an external processing device, such as, for example, external processing device 22 shown and described with respect to FIG. 2. In some embodiments, the inductive coil 54 can also inductively receive power from the external processing device to power the electronic components of the multipart sensing assembly 56.

Figure 6:
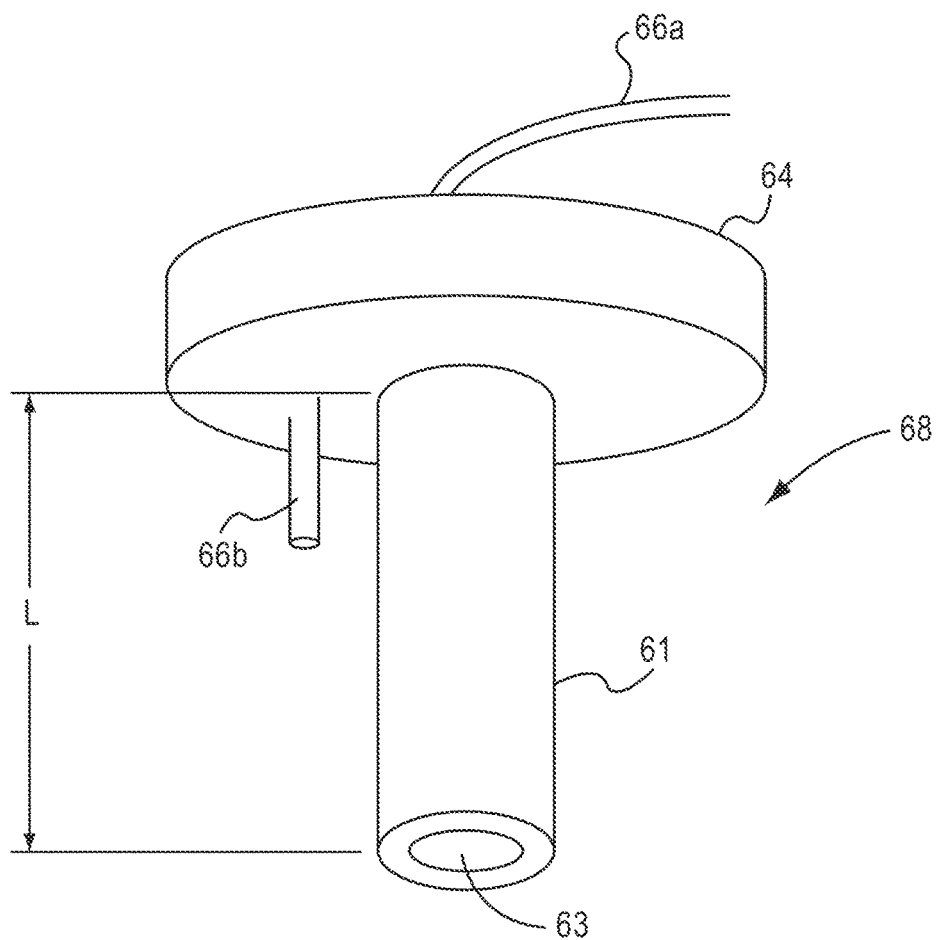
FIG. 6 illustrates an anchoring mechanism, according to an embodiment.

FIG. 6 illustrates another design of an anchoring mechanism as a bolt-shaped anchoring mechanism 68 according to an embodiment. The anchoring mechanism 68 includes a cylindrical portion 61 defining a cavity 63 for receiving and/or maintaining a sensing unit/wireless transceiver assembly in an orientation in which the sensing unit is exposed to the biological environment (e.g. a heart chamber). In some embodiments, a length L of the cylindrical portion 61 is selected depending on the thickness of the implantation site, such as a wall of a heart chamber. The heart wall thickness can be estimated prior to selecting the appropriate bolt size based on known procedures such as echocardiogram, computed tomography, MRI, a pressure sensitive needle, or observation of the patient's size and weight. The anchoring mechanism 68 further includes a button portion 64 configured to substantially occlude its implantation site. Similarly stated, the size, shape, and surface of the anchoring mechanism 68 or the button portion alone can be optimized to increase frictional contact with the implantation site. In some embodiments, the button portion may includes means for securing the anchor to the body including, for example and without limitation, sutures, pins, screws, glue, and/or the like. The anchoring mechanism 68 can also includes device connectors 66*a*, 66*b* for tethering or connection to other devices, such as, for example, a catheter, VAD, pacemaker, other sensors and/or anchoring mechanisms of other sensors.

In some embodiments, placement of a sensing unit/wireless transceiver or a sensing assembly (e.g. the cylindrical assembly 36 of FIG. 3) in the cavity 63 can be secured by a tight fit mechanism. In some embodiments, a biocompatible glue or epoxy is employed to secure the fit. In other embodiments, any other suitable mechanism can be used including, for example, pins that can be bent permanently upon exposure to higher temperatures.

Figures 7A, 7B:
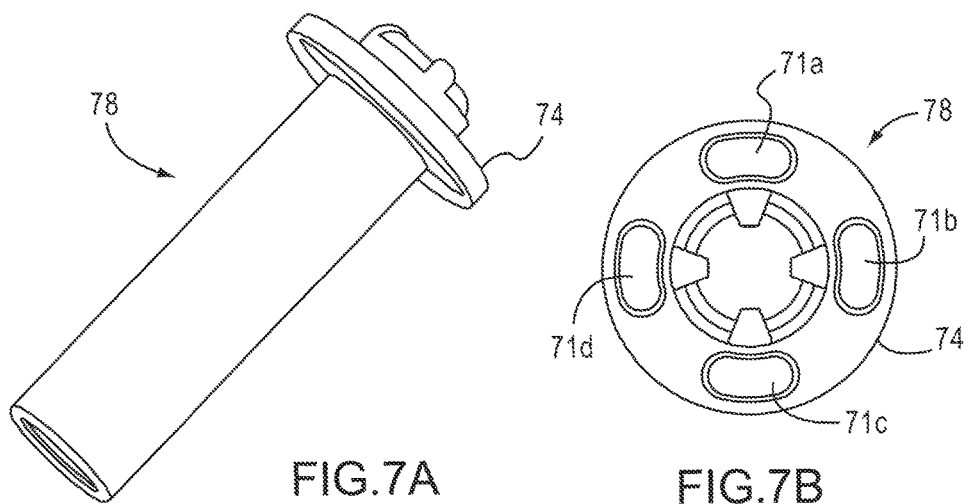
FIG. 7A illustrates an anchoring mechanism, according to an embodiment.
FIG. 7B is a top view of the anchoring mechanism of FIG. 7A.
Figure 7C:
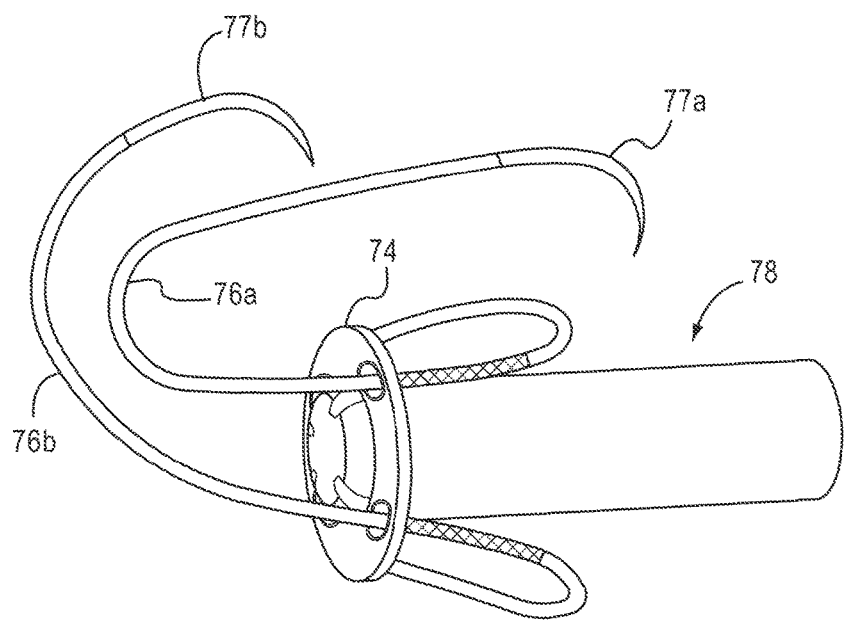
FIG. 7C is a side view of the anchoring mechanism of FIG. 7A with sutures.

FIGS. 7A-7C illustrate another design of a bolt-shaped anchoring mechanism 78, and more specifically illustrate a sensor that can be suitable to be sutured in place, for example, in a heart wall of a patient. The suturing procedure can be performed during and/or be required during a surgery such as, for example, an open chest surgery, minimally invasive surgery, trans-catheter surgery, hybrid surgery, and/or the like. For example, in a trans-catheter approach, a sensor having the anchoring mechanism 78 is delivered to an implantation site via a catheter (not shown) and implanted or otherwise fixed in the implantation site using sutures passing through holes 71*a*-71*d* of a button portion 74 of the anchoring mechanism. In some embodiments, trans-catheter or percutaneous delivery may use an anchor made at least partly from shape memory alloys (e.g. nitinol, or NiTi). Examples of suitable nitinol-based anchors may be found in U.S. Pat. No. 7,634,319 titled "Method and Anchor for Medical Implant Placement and Method of Anchor Manufacture" the disclosure of which is incorporated by reference herein in its entirety.

In some embodiments, after a cardiac device is implanted and/or after a sugary is completed, a delivery sheath or catheter used in the process can be subsequently used for parachuting an implantable sensor into its implantation site (for example in the heart wall) and then tightening preloaded sutures (or bands or other similar attachment methods) in order to fix and/or retain the sensor in its proper place. In some embodiments, the implantation site of the sensor is a surgical site. Such a method allows the sensor to be in close proximity to the surgical site.

A variety of methods can be used to deliver the sensor and place it in its implantation site. In some embodiments, such a method can include using a standard delivery sheath or catheter and introducing the sensor through a short feeder in order to place the sensor inside the site. In some embodiments, a specially designed sheath can be used at the beginning of the main operation in order to allow easier delivery and closure of the site after the main operation is completed. In some embodiments, another sheath of smaller caliber is placed coaxially inside the original delivery sheath and the smaller sheath is used for delivery and placement of the sensor. In some embodiments, the device delivery and implantation of the sensor can be compatible with the main operation in a way that adding the sensor as a complimentary task results in minimum or no added risk, (the risk of the main operation is higher), and a minimal amount of additional time.

In some embodiments, and as best illustrated in FIG. 7C, bands 76*a*, 76*b* with "shark's teeth" 77*a*, 77*b* can be employed, such that the bands lock automatically into holes 71*a*-71*d* when pulled. In another example (not shown), double purse sutures and double rail sutures are placed in the catheter and the anchoring mechanism 78 is loaded onto the rail sutures. Then, the sensor of the anchoring mechanism 78 is parachuted through the delivery sheath or catheter. The purse sutures are released and the sensor is inserted into the heart wall using the anchoring mechanism 78. The purse and rail sutures are then tightened. In some embodiments, the rail sutures can be pre-mounted into the holes 71*a*-71*b* of the anchoring mechanism 78. This results in a shorter implantation time since the surgeon does not need to load the implant on the sutures, and has two instead of four free suture ends (and needles) to manage during surgery. Pre-mounting the sutures can also reduce the risks associated with mixing the lines belonging to different sutures, and/or require the tightening of one knot instead of two.

Figure 8:
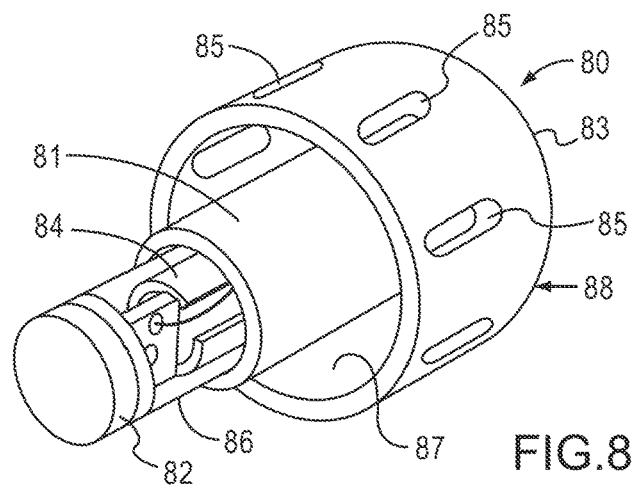
FIGS. 8 and 9 illustrate sensors, according to embodiments.

FIG. 8 illustrates another design of a sensor 80 having a capacitive sensing unit 82 and an inductive coil 84 inside a housing 86. In some embodiments, these components of sensor 80 are structurally and/or functionally similar to the cylindrical sensing assembly 36 of FIG. 3. The sensor 80 also includes a knob-shaped anchoring mechanism 88 having an inner cylindrical component 81 for holding the housing 86, an outer cylindrical component 83 defining one or more of apertures 85 and a cavity 87. As described above, the apertures 85 can be used for inserting sutures for implanting the sensor 80.

Figure 9:
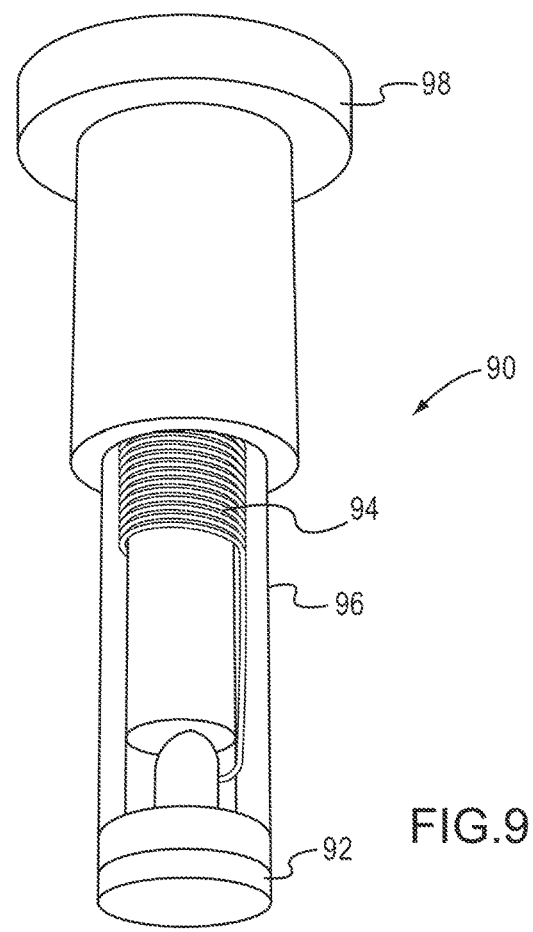

FIG. 9 illustrates a sensor 90 including a housing 96 for a capacitive sensing unit 92 and an inductive coil 94. In some embodiments, these components of sensor 90 are structurally and/or functionally similar to the cylindrical sensing assembly 36 of FIG. 3. The sensor 90 further includes a cylindrical anchor 98 for holding and/or retaining the housing 96. In some embodiments, the anchor 98 is structurally and/or functionally similar to the anchoring mechanism 68 of FIG. 6.

Figure 10:
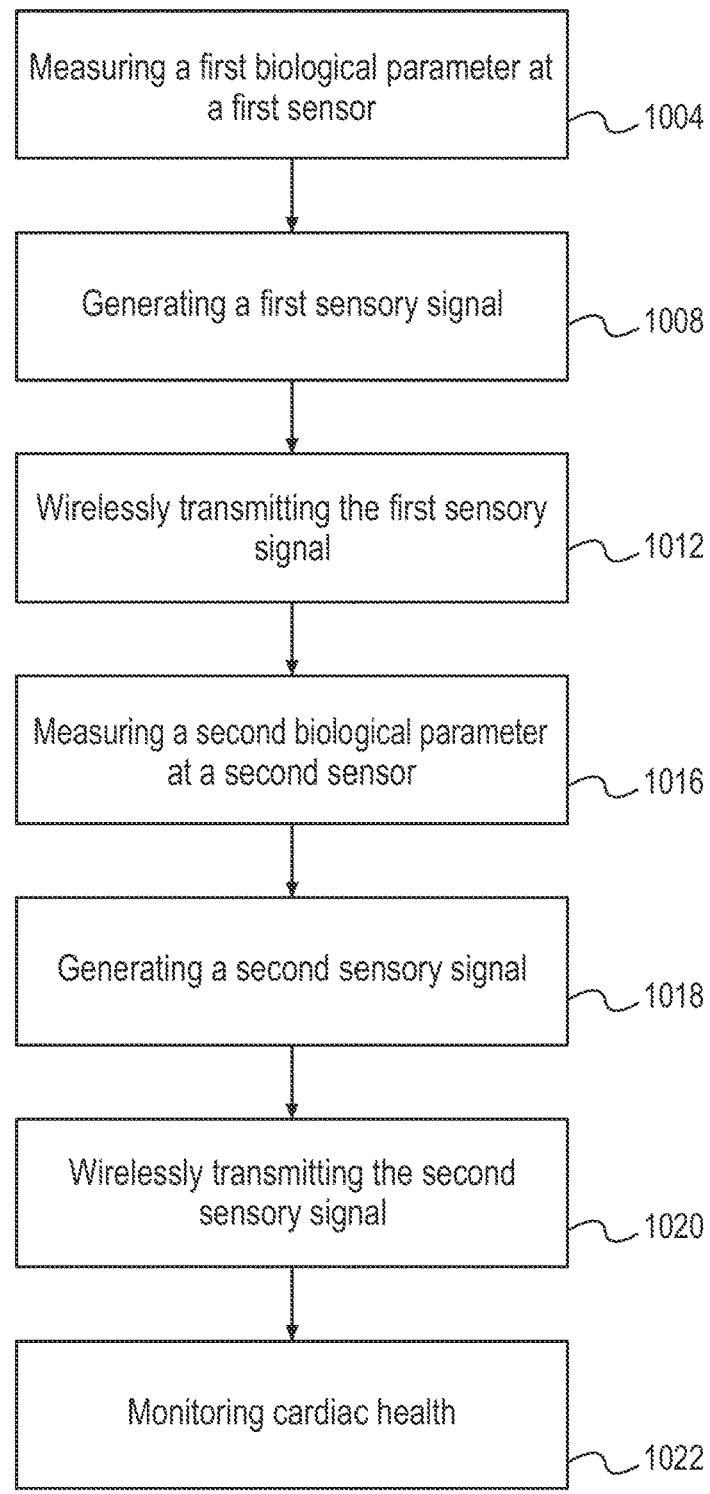
FIG. 10 is a flowchart illustrating a method of cardiac monitoring, according to an embodiment.

FIG. 10 illustrates a method according to an embodiment and is described herein, for example, with reference to the system 20 of FIG. 2. At 1004, a first biological parameter or a first set of biological parameters (e.g. pressure and/or temperature) is measured at a first sensor (e.g. sensor 10*a*) of the sensors 10*a*-10*n*. At 1008, a first sensory signal is generated by the first sensor 10*a* that is associated with the first biological parameter, and can include a value of the first biological parameter(s). At 1012, the first sensory signal is wirelessly transmitted, for example, by the first sensor 10a to the external processing device 22. At 1016, a second biological parameter or a second set of biological parameters is measured at a second sensor (e.g. sensor 10b) of the sensors 10a-10n. The first and second biological parameters can be the same or different, and can include blood pressure, temperature, blood pH, conductivity, dielectric constant, chemical concentration, gas content (e.g. oxygen), a metabolite (e.g. glucose), and/or the like. At 1018, the second sensory signal is generated by the second sensor 10b that is associated with the measurement of the second biological parameter. At 1020, the second sensory signal is wirelessly transmitted by the second sensor 10b to, for example, the external processing device 22. At 1022, the external processing device 22 monitors cardiac health as a function of the received sensory signals. In some embodiments, the monitored cardiac health is associated with the implanted device 24, and/or a surgery, as described in detail above.

Figure 11:
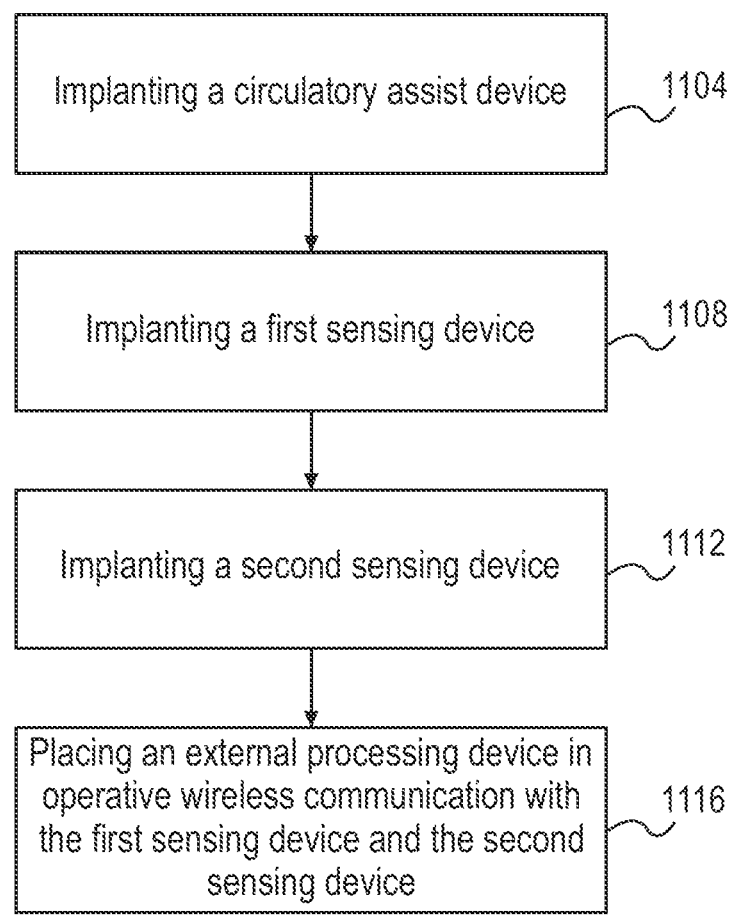
FIG. 11 is a flowchart illustrating a surgical method, according to an embodiment.

FIG. 11 illustrates an approach to monitoring cardiac health associated with a medical device (e.g., a circulatory assist device, as illustrated), and is described herein with reference to the system 20 of FIG. 2, where the implanted device 24 represents the medical device (e.g. a circulatory assist device such as a VAD). At 1104, the circulatory assist device 24 is implanted. At 1108 and 1112, at least first and second sensing devices (e.g. sensors 10a, 10b respectively from the sensors 10a-10n) are also implanted. In some embodiments, first and second sensing devices 10a, 10b are implanted during the same procedure in which the circulatory assist device 24 is implanted. In some embodiments, at least one of first and second sensing devices 10a, 10b is implanted in the same heart chamber and/or heart wall in which the circulatory assist device 24 is implanted. For example, in some embodiments, the circulatory assist device 24 can be a replacement mitral valve, and the first and second sensing devices 10a, 10b can be implanted on either side of the mitral valve in the wall of the LA, and in sensory communication with the LA.

In some embodiments, step 1104 results in the formation of a surgical site on the patient. In some embodiments, the surgical site includes an aperture to be closed for recovery, and at least one or steps 1108, 1112 results in one of the sensors 10a, 10b being selected for implantation in the surgical site during step 1104. As such, at least one of the sensors 10a, 10b can be used to occlude the aperture.

At 1116, the external processing device 22 is placed in wireless communication with the sensing devices 10a, 10b. In some embodiments, the external processing device employs the received sensory signals from the sensing devices 10a, 10b to monitor, power, and/or control the medical device 24. In some embodiments, at least part of the function of the external processing device 22 is performed by and/or integrated into the implanted device 24. In some embodiments, the external processing device 22 and the implanted device 24 may be a single device. In some embodiments, the external processing device is integrally formed with another implanted device (not shown) different from the implanted device 24.

In some embodiments, implantable wireless sensors are used as companion devices to cardiac operations. The implantation of the wireless sensors can be a secondary procedure during a cardiac operation. Adding the implant as a complimentary task results in minimum or no added risk since the risk of the main cardiac operation is higher, and a minimum amount of additional time is required to implant the sensors. Using implantable sensors as a companion to a cardiac operation can be useful in cases where a minimally invasive system is needed for monitoring cardiac parameters, such as cardiac pressures, after the cardiac operation. A cardiac monitoring system using such pressure sensors can provide physicians with a substantially real-time, substantially continuous, fast, safe, effective, and highly accurate tool for cardiac monitoring applications. In some embodiments, the pressure sensors can also be part of or attached to another implanted system, including, for example, pacemakers, LVADs, RVADs, BiVADs, ICDs, and/or the like.

In some cardiac operations, an incision or a surgical site (e.g., an aperture) is made in a portion of the heart in order to allow either a delivery sheath, a catheter, or other instrument to enter the heart. After the operation, when the sheath or catheter or instrument is retrieved, the surgical site needs to be closed. Instead of using traditional methods (for example suturing the site), the proposed implantable wireless sensor can be placed, for example, inside the surgical site and used to both close the surgical site and to provide sensing capabilities, for monitoring, for example, cardiac pressures. In another example, the surgical site can be used as a pass-though for access to an implantation site for the sensor to which access might have been otherwise challenging. After the sensor is installed, the surgical site may be closed by any suitable means, for example, by implanting another sensor in the surgical site as described above. Similarly stated, the surgical site defined during the surgery serves as an implantation site for a sensor and/or as a pass-through for a sensor. In embodiments where the implantable sensor is used to close the site after a cardiac surgery, an intraoperative epicardial echocardiography or another suitable procedure can be used for wall thicknesses assessment at the proposed implantation sites to determine the required length of the implantable sensor.

In some embodiments, the wireless sensor is an integrated part of another medical device, for example attached to a pacemaker, VAD, valve or shunt. Based on the specific device, the wireless sensor can be attached and anchored to a part of the device such that it is in contact with the blood or other physiological environment to be monitored. For such devices, the attachment method of the sensor (with or without an anchoring mechanism) to the device can depend on the device and/or application.

Figure 12A:
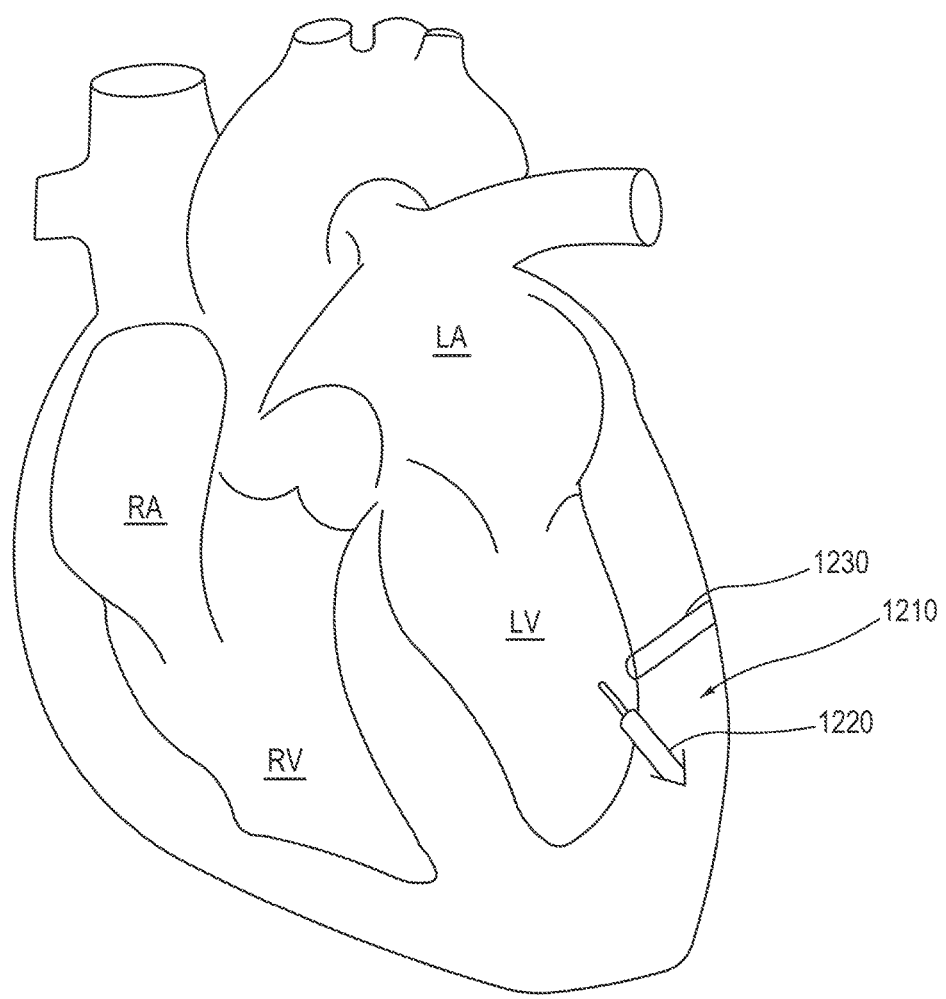
FIGS. 12A and 12B illustrate a cardiac monitoring system in use, according to an embodiment.
Figure 12B:
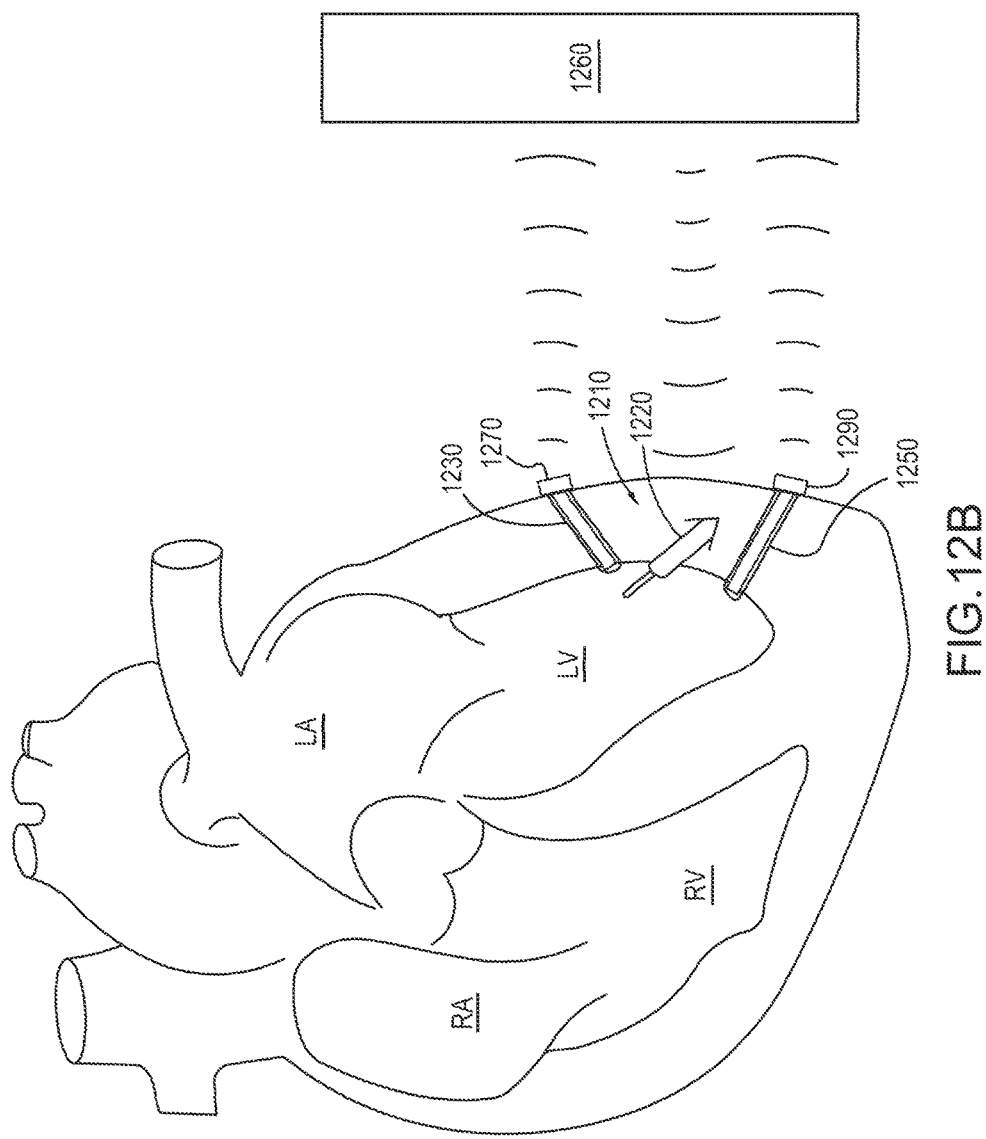

FIGS. 12A-12B illustrate the use of a cardiac monitoring system in a heart of a patient according to an embodiment, and is described herein, for example, with reference to the system 20 of FIG. 2. As best seen in FIG. 12A, a cardiac device 1220 (i.e. similar to the implanted device 24) is implanted in a wall of the left ventricle chamber LV of the heart 1210 of a patient, and/or a surgery is performed (not shown) such as, for example, a transapic TAVI operation. Implantation of the cardiac device and/or performing the surgery results in a surgical site 1230 (e.g., an aperture created to deliver the cardiac device 1220 to the LV, an iatrogenic hole, etc.) to be sealed after the implantation is complete. FIG. 12B illustrates the further implantation of a sensor 1270 (e.g., similar to sensor 10a) in the surgical site 1230 previously defined, and the implantation of a sensor 1290 (e.g., similar to sensor 10b) in another implantation site 1250. Sensors 1270, 1290 sense pressure in the LV, thereby monitoring performance of the cardiac device. The sensed pressure data is wirelessly transmitted to an external processing device 1260 (e.g., the external processing device 22), which can monitor the cardiac device, and alarm the user when unusual pressure values are detected in the left ventricle 1220. In some embodiments (not shown), implantation site 1250 (containing the sensor 1290) may be formed in the RA, LA, or LV instead, allowing measurement of pressure in the associated heart chamber. In some embodiments, device 1220 is an LVAD, and sensors 1270, 1290 are implanted in the LA, RV respectively. In some embodiments, device 1220 is an LVAD, and sensors 1270, 1290 are implanted in the LV, RV respectively. In some embodiments, device 1220 is an LVAD, and sensors 1270, 1290 are implanted in the LV, RA respectively. The use of multiple sensors in multiple locations generally provides benefits of redundancy, reduced error, and a more comprehensive, biologically relevant measurement of the spatial distribution of parameter values.

While shown and described with respect to FIGS. 12A-12B as implanting multiple sensors in a single area (e.g., LV) within a heart, in other embodiments, multiple sensors can be implanted in different areas of the heart. For example, a first sensor can be implanted within the LV of the heart and a second sensor can be implanted within the RA of the heart. In such embodiments, operation of different portions of the heart can be monitored by an external processing device. Receiving values from different portions of the heart can be used to more comprehensively monitor the operation of the heart.

Figure 13:
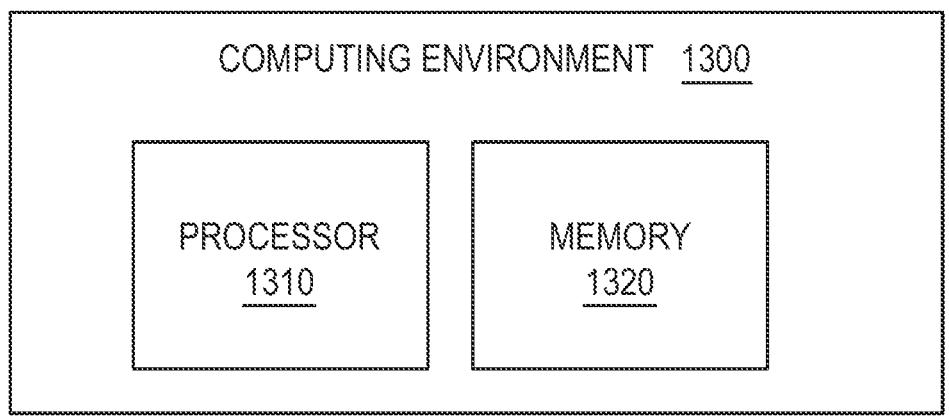
FIG. 13 is an exemplary computing environment, according to an embodiment.

In some embodiments of the various components described herein (e.g. the sensing unit 12, the wireless transceiver 14, the external processing device 22, the implanted device 24, linking elements such as the connector 33, and all combinations, subsystems thereof can include a computing environment 1300 (see FIG. 13) having at least a processor 1310 and a memory 1320 for performing some or all of the stated functionality. For example, in some embodiments, the connector 33 of FIG. 3 can include a computing environment 1300 that can buffer the sensory signals received from the sensing unit 32 in the memory 1320 based on an algorithm stored in memory 1320 and executed by processor 1310.

In some embodiments, the processor 1310 can be a general purpose processor, a Field Programmable Gate Array (FPGA), an Application Specific Integrated Circuit (ASIC), a Digital Signal Processor (DSP), and/or the like. In some embodiments, the memory 1320 can be, for example, a random access memory (RAM), a memory buffer, a hard drive, a database, an erasable programmable read-only memory (EPROM), an electrically erasable read-only memory (EEPROM), a read-only memory (ROM) and/or the like.

The computing environment 1300 can be operable to execute computer code to perform the disclosed functionality. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Java, C++, or other programming languages (e.g., object-oriented programming languages) and development tools. Additional examples of computer code include, but are not limited to, control signals, encrypted code, and compressed code. Such computer code can also be referred to as a computer program and some embodiments can be in the form of a computer program.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The various embodiments described herein should not to be construed as limiting this disclosure in scope or spirit. It is to be understood that no limitation to the scope of the disclosure is intended thereby. It is to be further understood that resort can be had to various other embodiments, modifications, and equivalents thereof which can suggest themselves to those skilled in the art without departing from the spirit of the present disclosure and/or scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A cardiac monitoring system, comprising:
   a plurality of sensors configured for implantation in a cardiovascular system of a user, each sensor from the plurality of sensors including:
   a sensing unit configured to be disposed in sensory communication with a location in the cardiovascular system for measuring a biological parameter in the location, said sensing unit configured to generate a sensory signal associated with the biological parameter;
   a button portion defining a distal side, a proximal side opposite the distal side, and a plurality of apertures configured to receive a suture for anchoring the sensing unit in sensory communication with the location, the plurality of apertures collectively having a cross-sectional area less than a cross-sectional area of the proximal side of the button portion;
   an elongate portion extending from the distal side of the button portion and having a diameter smaller than a diameter of the button portion, the button portion being configured to occlude an aperture defined by the cardiovascular system and having a width sufficient to receive the elongate portion, the elongate portion defining a cavity in which the sensing unit is disposed; and a wireless transceiver configured to receive the sensory signal from the sensing unit and configured to wirelessly transmit the sensory signal to an external processing device disposed outside a body of the user such that the external processing device monitors, based on the sensory signal received from the plurality of sensors, cardiac health associated with at least one of an implanted device or a surgery.

2. The system of claim 1, wherein the sensing unit is configured to be disposed in sensory communication with at least one of a heart chamber, a heart wall, a vein, or an artery.

3. The system of claim 1, wherein:
at least one sensor from the plurality of sensors does not communicate a sensory signal to a remaining sensor from the plurality of sensors; and
at least one sensor from the plurality of sensors does not directly communicate a sensory signal to the implanted device.

4. The system of claim 1, wherein:
at least one sensor from the plurality of sensors directly communicates a sensory signal to the implanted device; and
the external processing unit directly communicates with the implanted device.

5. The system of claim 1, wherein at least one sensor from the plurality of sensors is a cylindrical sensor, the cylindrical sensor includes a hollow cylindrical anchor including the button portion and is configured to anchor the cylindrical sensor to the location.

6. The system of claim 5, wherein a length of the cylindrical anchor is selected as a function of a wall thickness of the aperture defined by the cardiovascular system.

7. The system of claim 1, wherein at least one sensor from the plurality of sensors is a multipart assembly sensor.

8. The system of claim 7, wherein:
the multipart assembly sensor has a multipart sensing assembly including at least a sensing subassembly and a non-sensing subassembly;
the sensing subassembly includes the sensing unit and the non-sensing subassembly includes the wireless transceiver;
the sensing subassembly is configured to be implanted within a heart of the user;
the non-sensing subassembly is configured to be placed outside the heart of the user; and
the sensing subassembly is configured to be at least one of mechanically coupled or electrically coupled to the non-sensing subassembly.

9. The system of claim 1, wherein each sensor from the plurality of sensors includes an anchoring mechanism for anchoring each sensor from the plurality of sensors to the location, said anchoring mechanism for each sensor from the plurality of sensors including at least one of a compression fit anchor, at least one bolt, at least one screw, a mesh portion, at least one stent, at least one spring, at least one stitch, or at least one expanding tine.

10. The system of claim 1, wherein the biological parameter monitored by each sensor from the plurality of sensors includes at least one of a blood pressure, a temperature, a blood pH, conductivity, a dielectric constant, a chemical concentration, a gas content, or a metabolite.

11. The system of claim 1, wherein the sensing unit of at least one sensor from the plurality of sensors is a capacitive sensing unit including at least one flexible electrode attached to a substrate and at least one rigid electrode formed on the substrate.

12. The system of claim 1, wherein the wireless transceiver of at least one sensor from the plurality of sensors is configured to receive, from an external powering device disposed outside the body of the user, a power signal for powering the at least one sensor.

13. The system of claim 12, wherein the wireless transceiver includes at least one induction coil configured to (1) transmit the sensory signal and (2) receive the power signal.

14. The system of claim 1, wherein:
the external processing device is configured to at least one of wirelessly monitor the plurality of sensors, wirelessly control the plurality of sensors, or wirelessly charge the plurality of sensors, and
the external processing device is configured to at least one of wirelessly monitor the implanted device or wirelessly control the implanted device.

15. The system of claim 1, wherein the implanted device is at least one of a ventricular assist device (VAD) or a replacement valve.

16. The method of claim 1, wherein the surgery includes at least one of a coronary artery bypass graft (CABG), a valve repair, a transcatheter aortic valve operation, a catheter-based operation, open chest surgery, interventional operation, catheter-based surgery, percutaneous operation, hybrid operation, or a minimally invasive surgery.

17. The system of claim 1, wherein the button portion defines a device connector extending from the button portion, the device connector configured to couple to a device otherwise physically separate from the button portion.

18. The system of claim 1, further comprising:
the suture, the suture having an anchor portion and an elongate portion, a portion of the elongate portion of the suture configured to be routed through the plurality of apertures, and the anchor portion defined such that the anchor portion is prevented from being routed through the plurality of apertures of the button portion.

19. The system of claim 18, wherein:
the anchor portion of the suture having a curved shape.

20. The system of claim 1, wherein each aperture from the plurality of apertures is configured to receive a different suture for anchoring the sensing unit in sensory communication with the location, the plurality of apertures spaced circumferentially about the button portion.

21. The system of claim 1, wherein the plurality of apertures are spaced circumferentially about the button portion, each aperture from the plurality of apertures being equidistant from a central longitudinal axis of the elongate portion.

22. The system of claim 1, wherein the plurality of apertures are spaced circumferentially and uniformly about the button portion.

23. The system of claim 1, wherein a device connector extends along a longitudinal axis substantially parallel to a longitudinal axis of the elongate portion, the device connector having a length less than a length of the elongate portion.

24. The system of claim 1, wherein a device connector extends from the distal side of the button portion.

25. The system of claim 1, wherein the wireless transceiver is disposed within the cavity defined by the elongate portion.

26. The system of claim 1, wherein the cavity is in fluidic communication with the location in the cardiovascular system when the sensing unit is disposed in sensory communication with the location.

27. A method, comprising:
    measuring a first biological parameter using a first sensor implanted in a wall of a first chamber of a heart of a user, the first sensor including (1) a button portion defining at least one aperture configured to receive a suture for anchoring the first sensor in sensory communication with the first chamber of the heart, (2) a device connector extending distally from a distal side of the button portion and configured to couple to a device otherwise physically separate from the first sensor, and (3) an elongate portion extending from the button portion;
    generating a first sensory signal associated with the first biological parameter;
    wirelessly transmitting, by the first sensor, the first sensory signal to an external processing device located outside the body of the user;
    measuring a second biological parameter at a second sensor implanted in a wall of a second chamber of the heart;
    generating a second sensory signal associated with the second biological parameter; and
    wirelessly transmitting, by the second sensor, the second sensory signal to the external processing device; and
    monitoring, based on at least one of the first sensory signal or the second sensory signal, cardiac health associated with at least one of an implanted device or a surgery.

28. The method of claim 27, wherein the implanted device does not directly receive the first sensory signal from the first sensor, the implanted device does not directly receive the second sensory signal from the second sensor.

29. The method of claim 27, wherein at least one of the first sensor or the second sensor is one of a cylindrical sensor, a flat sensor, or a multipart assembly sensor including a sensing subassembly and a non-sensing subassembly, the first sensor being selected as a function of the wall of the first chamber of the heart.

30. The method of claim 27, wherein the first biological parameter and the second biological parameter each include at least one of a blood pressure, a temperature, a blood pH, a conductivity, a dielectric constant, a chemical concentration, a gas content, or a metabolite.

31. The method of claim 27, further comprising receiving, at the first ensor a power signal from the external processing device for powering the first sensor.

32. The method of claim 27, wherein the monitoring includes monitoring, at the external processing device, at least one of:
    a datum associated with the first sensory signal;
    a datum associated with the second sensory signal;
    a datum associated with the implanted device; or
    a datum associated with the monitored cardiac health.

33. The method of claim 27, further comprising at least one of:
    wirelessly monitoring at least one of the first sensor or the second sensor;
    wirelessly controlling at least one of the first sensor or the second sensor; or
    wirelessly charging at least one of the first sensor or the second sensor, and at least one of:
    wirelessly monitoring the implanted device;
    wirelessly controlling the implanted device; or
    wirelessly charging the implanted device.

34. The method of claim 27, further comprising implanting the first sensor via the suture placed in one or more placement catheters during at least one of implantation of the implanted device or the surgery.

35. The method of claim 34, further comprising pre loading the first sensor onto the suture prior to the at least one of implantation of the implanted device or the surgery.

36. The method of claim 35, wherein the suture includes a rail suture and a purse suture, said pre-loading including loading the first sensor onto the rail suture.

37. The method of claim 27, wherein a surgical site is formed due to at least one of implantation of the implanted device or the surgery, the method further comprising at least one of:
    implanting at least one of the first sensor or the second sensor in the surgical site; or
    passing at least one of the first sensor or the second sensor through the surgical site for implantation in a site different from the surgical site.

38. The method of claim 27, wherein the implanted device is at least one of a ventricular assist device (VAD) or a replacement valve.

39. A method, comprising:
    implanting in a patient a medical device;
    implanting in a first location of a cardiovascular system of the patient a first sensing device in sensory communication with the first location, the first sensing device operable to measure a first biological parameter in the first location relevant to a performance of the medical device and to wirelessly transmit via a wireless transmitter a first signal representative of the first biological parameter to an external processing, device disposed outside a body of the patient, the first sensing device including a button portion and an elongate portion extending from the button portion and having a diameter smaller than a diameter of the button portion, the elongate portion defining a cavity in which the wireless transmitter is disposed, the button portion being configured to occlude an aperture defined by the cardiovascular system and having a width sufficient to receive the elongate portion, the button portion defining a plurality of apertures each configured to receive a suture for anchoring the first sensing device in sensory communication with the first location, the plurality of apertures collectively having a cross-sectional area less than a cross-sectional area of a proximal side of the button portion;
    implanting in a second location of the cardiovascular system of the patient a second sensing device in sensory communication with the second location, the second sensing device operable to measure a second biological parameter in the second location relevant to the performance of the medical device and to wirelessly transmit a second signal representative of the second biological parameter to the external processing device; and
    placing into operative wireless communication with each of the first sensing device and the second sensing device the external processing device, the external processing device operable to monitor operation of the medical device based on the first signal and the second signal.

40. The method of claim 39, wherein at least one of the first sensing device or the second sensing device is a pressure sensor, the implanting the first sensing device includes implanting the first sensing device during implantation of the medical device.

41. The method of claim 39, wherein the first location and the second location each include at least one of a wall of the left atrium, a wall of the right atrium, a wall of a left ventricle, a wall of a right ventricle, an interatrial septum, an interventricular septum, an atrioventricular septum, a wall of a vein, or a wall of an artery.

42. The method of claim 39, wherein the implanting the first sensing device in the first location includes implanting the first sensing device in a surgical site formed due to implantation of the medical device.

43. The method of claim 39, wherein the medical device is at least one of a ventricular assist device (VAD) or a replacement valve.

44. A cardiac monitoring system, comprising:
a plurality of sensors configured for implantation in a cardiovascular system of a user, each sensor from the plurality of sensors including:
a sensing unit configured to be disposed in sensory communication with a location in the cardiovascular system for measuring a biological parameter in the location, said sensing unit configured to generate a sensory signal associated with the biological parameter;
a button portion defining at least one aperture configured to receive a suture for anchoring the sensing unit in sensory communication with the location;
a device connector extending from the button portion and configured to couple to a device otherwise physically separate from that sensor;
an elongate portion extending from the button portion and having a diameter smaller than a diameter of the button portion, the button portion being configured to occlude an aperture defined by the cardiovascular system and having a width sufficient to receive the elongate portion; the elongate portion and the device connector both extending distally from a same surface of the button portion; and
a wireless transceiver configured to receive the sensory signal from the sensing unit and configured to wirelessly transmit the sensory signal to an external processing device disposed outside a body of the user,
such that the external processing device monitors, based on the sensory signal received from the plurality of sensors, cardiac health associated with at least one of an implanted device or a surgery.

45. The system of claim 44, wherein the elongate portion extends from the button portion in a direction substantially parallel to a direction in which the device connector extends from the button portion.

46. The system of claim 44, wherein at least one of the sensing unit or the wireless transceiver is disposed in a cavity defined by the elongate portion.

* * * * *